United States Patent
Goluch et al.

(10) Patent No.: US 10,316,348 B2
(45) Date of Patent: Jun. 11, 2019

(54) DIAGNOSTIC SYSTEM AND PROCESS FOR RAPID BACTERIAL INFECTION DIAGNOSIS

(71) Applicant: Northeastern University, Boston, MA (US)

(72) Inventors: Edgar D. Goluch, Somerville, MA (US); Hunter J. Sismaet, Boston, MA (US); Thaddaeus A. Webster, Exeter, NH (US)

(73) Assignee: Northeastern University, Boston, MA (US)

( * ) Notice: Subject to any disclaimer, the term of this patent is extended or adjusted under 35 U.S.C. 154(b) by 0 days.

(21) Appl. No.: 15/511,735

(22) PCT Filed: Sep. 16, 2015

(86) PCT No.: PCT/US2015/050412
§ 371 (c)(1),
(2) Date: Mar. 16, 2017

(87) PCT Pub. No.: WO2016/044417
PCT Pub. Date: Mar. 24, 2016

(65) Prior Publication Data
US 2017/0247739 A1    Aug. 31, 2017

Related U.S. Application Data

(60) Provisional application No. 62/051,099, filed on Sep. 16, 2014, provisional application No. 62/215,379, filed on Sep. 8, 2015.

(51) Int. Cl.
*C12Q 1/12* (2006.01)
*C12Q 1/04* (2006.01)
(Continued)

(52) U.S. Cl.
CPC .............. *C12Q 1/12* (2013.01); *A61K 31/496* (2013.01); *A61K 38/12* (2013.01);
(Continued)

(58) Field of Classification Search
None
See application file for complete search history.

(56) References Cited

U.S. PATENT DOCUMENTS

6,245,735 B1   6/2001 Pier
2013/0022578 A1   1/2013 Newman et al.

FOREIGN PATENT DOCUMENTS

WO   2012/149058 A2   11/2012
WO   2013103780 A1   7/2013
(Continued)

OTHER PUBLICATIONS

Webster et al., Lab Chip, 2012, 12, 5195-5201.*
(Continued)

*Primary Examiner* — Karl J Puttlitz
(74) *Attorney, Agent, or Firm* — Arent Fox LLP

(57) ABSTRACT

Methods and devices for monitoring the viability of a biofilm comprising *Pseudomonas Aeruginosa* bacteria are provided by detecting pyocyanin. The invention relates to electrochemical methods and devices that offer a simple and inexpensive alternative for immediate identification of bacterial infection due to the presence of *Pseudomonas aeruginosa*. In some embodiments, an inexpensive, disposable electrochemical sensor can be used to rapidly screen for the presence of *P. aeruginosa* in clinical wound effluent samples.

23 Claims, 22 Drawing Sheets

(51) Int. Cl.
| | |
|---|---|
| C12Q 1/18 | (2006.01) |
| G01N 27/48 | (2006.01) |
| A61K 31/496 | (2006.01) |
| A61K 38/12 | (2006.01) |
| B01L 3/00 | (2006.01) |
| G01N 27/327 | (2006.01) |
| G01N 33/487 | (2006.01) |
| C12M 1/34 | (2006.01) |
| C12Q 1/02 | (2006.01) |
| C12Q 1/22 | (2006.01) |

(52) U.S. Cl.
CPC ......... *B01L 3/502715* (2013.01); *C12M 1/34* (2013.01); *C12Q 1/02* (2013.01); *C12Q 1/04* (2013.01); *C12Q 1/18* (2013.01); *C12Q 1/22* (2013.01); *G01N 27/327* (2013.01); *G01N 27/48* (2013.01); *G01N 33/48735* (2013.01); *B01L 3/5027* (2013.01); *B01L 2300/02* (2013.01); *B01L 2300/0636* (2013.01); *B01L 2300/0645* (2013.01); *G01N 33/48707* (2013.01); *G01N 2333/21* (2013.01)

(56) References Cited

FOREIGN PATENT DOCUMENTS

| WO | 2014015333 | A1 | | 1/2014 |
| WO | 20140153333 | | * | 1/2014 |
| WO | 2015031798 | A1 | | 3/2015 |

OTHER PUBLICATIONS

Webster et al., Nano Life vol. 3, No. 1, 2013.*
Nebster T et al. Improved monitoring of P. aeruginosa on agar plates. Anal. Methods, 2015, 7, pp. 7150-7155.
Lau G et al. The role of pyocyanin in Pseudomonas aeruginosa infection. Trends Mol Med, 2004, 10(12):599-606.
Pires L et al. Online monitoring of biofilm growth and activity using a combined multi-channel impedimetric and amperometric sensor. Biosens Bioelectron, 2013, 47:157-163.
Webster T et al. Electrochemical Detection of Pyocyanin in Nanochannels with Integrated Palladium Hydride Reference Electrodes, Lab Chip, 12, pp. 5195-5201, 2012.
Webster T et al. Electrochemical detection of Pseudomonas aeruginosa in human fluid samples via pyocyanin. Biosens Bioelectron, 2014, 60:265-270.
Hoyle, B.D., et al., "Pseudomonas aeruginosa Biofilm as a Diffusion Barrier to Piperacillin", Antimicrobial Agents and Chemotherapy, Sep. 1992, 36:2054-2056.
Stewart, P.S., "Diffusion in Biofilms", Journal of Bacteriology, Mar. 2003, 185:1485-1491.
Dotsch, et al., "The Pseudomonas aeruginosa Transcriptome in Planktonic Cultures and Static Biofilms Using RNA Sequencing" PLoS One, Feb. 2012, 7:2.
A.C. Ward, et al., "Pseudomonas aeruginosa Can Be Detected in a Polymicrobial Competition Model Using Impedance Spectroscopy with a Novel Biosensor", PLOS One, Mar. 2014, vol. 9, Iss. 3, e91732.
D.L. Bellin, et al., "Integrated circuit-based electrochemical sensor for spatially resolved detection of redox-active metabolites in biofilms", Nature Communications, Feb. 10, 2014, vol. 5.
M.C. Macia, et al., "Antimicrobial susceptibility testing in biofilm-growing bacteria", Clinical Microbiology and Infection, Oct. 2014, vol. 20, No. 10, pp. 981-990.
E.K. Manavathu, et al., "Development and antimicrobial susceptibility studies of in vitro monomicrobial and polymicrobial biobilm models with Aspergillus fumigatus and Pseudomonas aeruginosa", BMC Microbiology, (2014), vol. 14, No. 53.

* cited by examiner

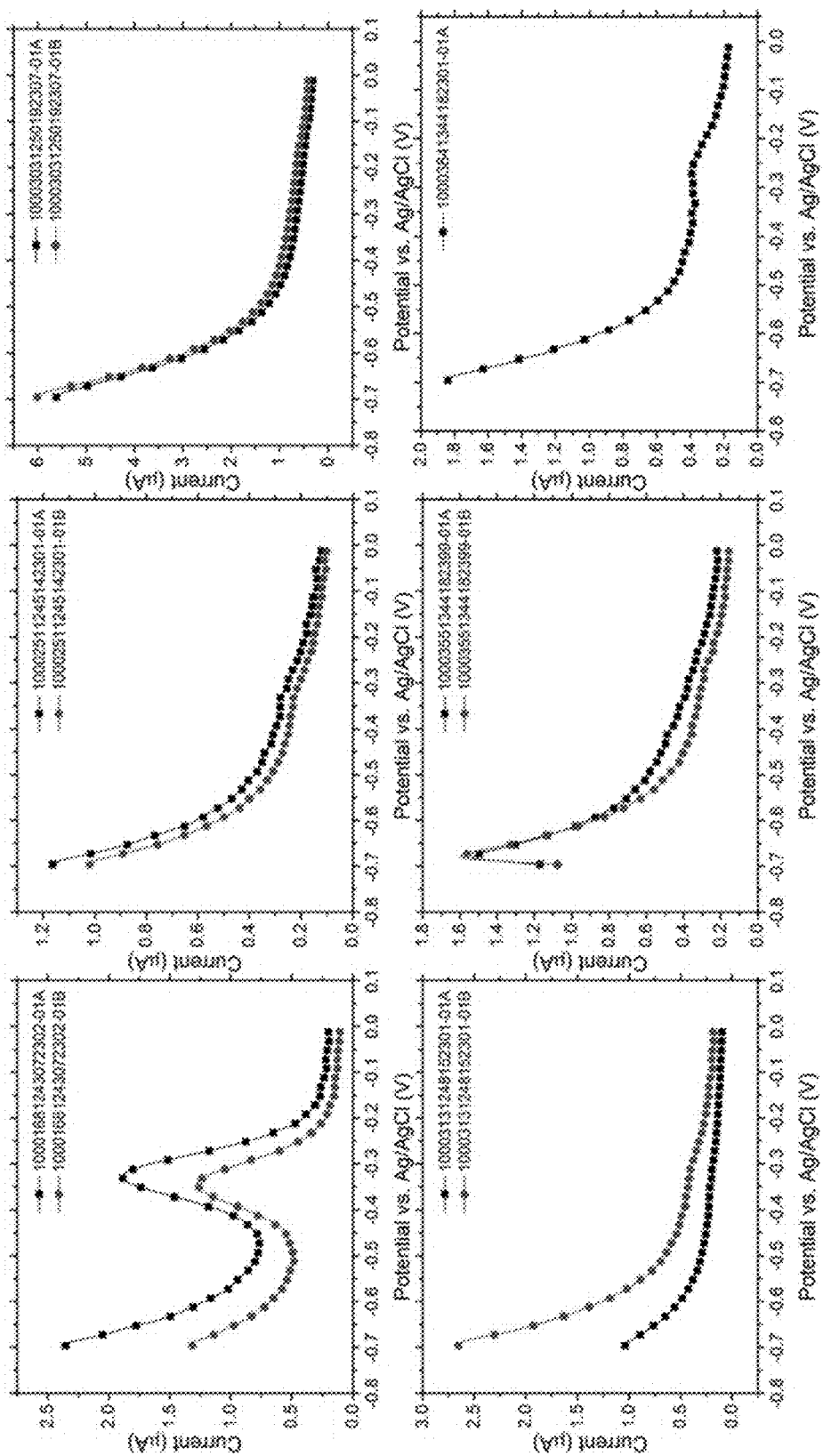
FIG. 3 1st Continuation

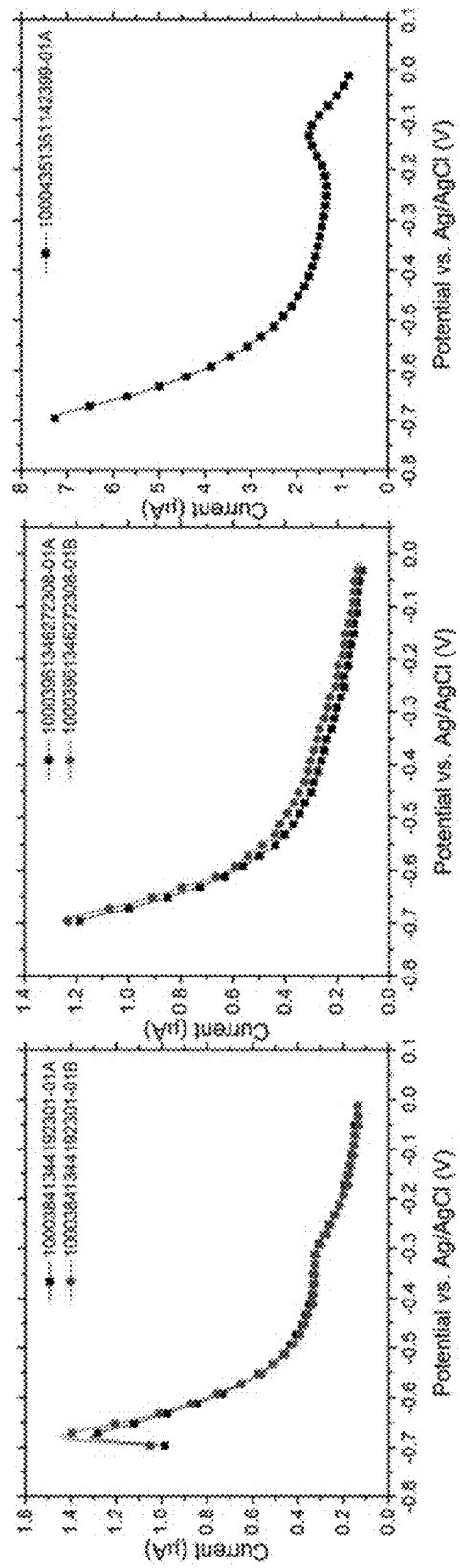
FIG. 3 2nd Continuation

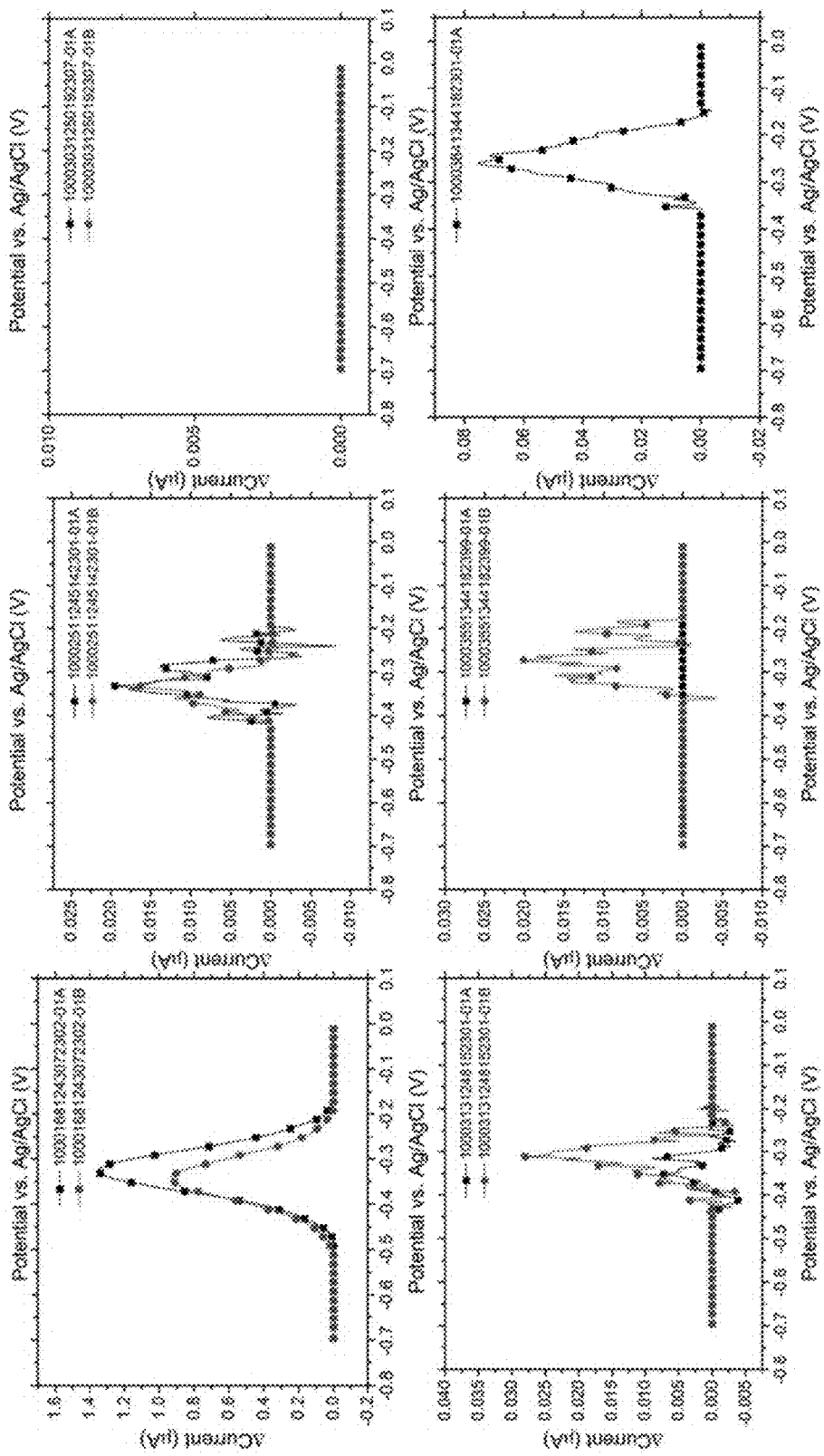
FIG. 4 1st Continuation

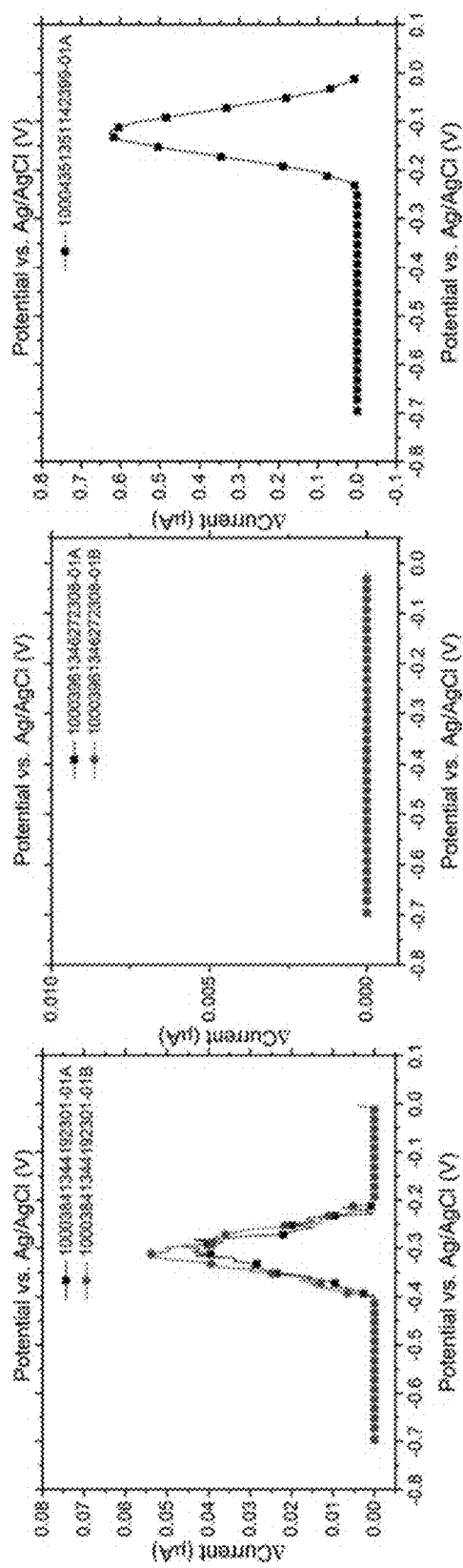
FIG. 4 2nd Continuation

DIAGNOSTIC SYSTEM AND PROCESS FOR RAPID BACTERIAL INFECTION DIAGNOSIS

CROSS REFERENCE TO RELATED APPLICATIONS

This application claims priority under 35 § 119(e) of U.S. Provisional Application No. 62/051,099 filed on Sep. 16, 2014, entitled "Diagnostic System and Process for Rapid Bacterial Infection Diagnosis", the disclosure of which is hereby incorporated by reference.

This application claims priority under 35 § 119(e) of U.S. Provisional Application No. 62/215,379 filed on Sep. 8, 2015, entitled "Diagnostic System and Process for Rapid Bacterial Infection Diagnosis", the disclosure of which is hereby incorporated by reference.

STATEMENT REGARDING FEDERALLY SPONSORED RESEARCH OR DEVELOPMENT

The invention was developed with financial support from Grant No. 1125535 from the National Science Foundation. The U.S. Government has certain rights in the invention.

BACKGROUND

For more than a century, the primary clinical identification method for bacterial infections has been plate cultures where bacteria are isolated and purified overnight using nutrient-based agar medium. Although rapid, automated instrumentation has been widely regarded as the next step towards advancing bacterial identification, these instruments still require a pure bacterial colony obtained from a plate culture and thus a lead time of at least 18-24 hours before any identification can be made. (Cherkaoui, A., et al., *Comparison of two matrix-assisted laser desorption ionization-time of flight mass spectrometry methods with conventional phenotypic identification for routine identification of bacteria to the species level*. J Clin Microbiol, 2010. 48(4): p. 1169-75. Holland, R. D., et al., *Rapid identification of intact whole bacteria based on spectral patterns using matrix-assisted laser desorption/ionization with time-of-flight mass spectrometry*. Rapid Communications in Mass Spectrometry, 1996. 10(10): p. 1227-1232.) Likewise, molecular diagnostics such as polymerase chain reaction require pure bacterial colonies and hours of processing. (Meng, J., et al., *Polymerase chain reaction for detecting Escherichia coli O157:H7*. Int J Food Microbiol, 1996. 32(1-2): p. 103-13.) As a result, rapid screens for clinically-relevant bacterial species have become an attractive alternative option for hospitals looking for more rapid point-of-care diagnostics. A rapid screen for *Pseudomonas aeruginosa* and other clinically-relevant bacteria would allow doctors to promptly switch from broad-spectrum antibiotics to specific directed therapies, lowering hospital expenditures, minimizing drug resistance, and improving patient care outcomes. (Trenholme, G. M., et al., *Clinical impact of rapid identification and susceptibility testing of bacterial blood culture isolates*. J Clin Microbiol, 1989. 27(6): p. 1342-5.)

Additionally, the ability to monitor the effect antibiotics have on bacteria is important for infection control. The conventional approach to determining antibiotic efficacy requires the creation of culture plates with the antibiotic cocktail of choice at a series of concentrations. (J. M. Andrews, *J. Antimicrob Chemother,* 2001, 48, 5-16.) After culturing (for 24 hours or longer, depending on the strain), the plates are visually inspected for growth. At a certain concentration, known as the minimum inhibitory concentration (MIC), no bacterial growth is observed. This concentration is then used to design an antibiotic schedule for the patient. This effective approach suffers from the use of large amounts of reagents required to produce the culture plates. Furthermore, these screens only measure the effectiveness of the antibiotic against planktonic cell growth; not removal of biofilms, which are commonly associated with infections and significantly more difficult to treat. (P. K. Singh, A. L. Schaefer, M. R. Parsek, T. O. Moninger, M. J. Welsh and E. P. Greenberg, *Nature,* 2000, 407, 762-764. C. F. Schierle, M. De la Garza, T. A. Mustoe and R. D. Galiano, *Wound Repair Regen,* 2009, 17, 354-359.)

An alternative is coupling microfluidics, to grow the bacteria, with antibiotic screens. Kim et al. (2012) utilized a microfluidic system to simultaneously expose biofilms of *Escherichia coli* to eight different concentrations of antibiotics on a single chip. (J. Kim, M. Hegde, S. H. Kim, T. K. Wood and A. Jayaraman, *Lab Chip,* 2012, 12, 1157-1163.) The smaller volumes, inherent in microfluidic devices, along with the ability to produce multiple concentration gradients provided a faster, cheaper alternative to current antibiotic susceptibility tests. By flowing antibiotics over the grown biofilms, researchers more closely simulated in vivo conditions. Many current microfluidic studies determine biofilm viability based on the presence of fluorescent proteins during exposure to antibiotics. (J. Kim, H. D. Park and S. Chung, Microfluidic approaches to bacterial biofilm formation, *Molecules,* 2012, 17, 9818-9834. K. P. Kim, Y. G. Kim, C. H. Choi, H. E. Kim, S. H. Lee, W. S. Chang and C. S. Lee, *Lab Chip,* 2010, 10, 3296-3299.) While these methods are certainly robust and promising, the fluorescent signal requires expensive optical equipment and genetically modified bacteria or selective labels. (L. Richter, C. Stepper, A. Mak, A. Reinthaler, R. Heer, M. Kast, H. Bruckl and P. Ertl, Lab Chip, 2007, 7, 1723-1731. H.-Y. N. Holman, R. Miles, Z. Hao, E. Wozei, L. M. Anderson and H. Yang, Anal Chem, 2009, 81, 8564-8570. Y. Yawata, K. Toda, E. Setoyama, J. Fukuda, H. Suzuki, H. Uchiyama and N. Nomura, J Biosci Bioeng, 2010, 110, 130-133. Y. Yawata, K. Toda, E. Setoyama, J. Fukuda, H. Suzuki, H. Uchiyama and N. Nomura, J Biosci Bioeng, 2010, 110, 377-380.) A cheaper and easier method of determining the relative amount of live cells in a biofilm under exposure to antibiotics can be achieved by monitoring the electrochemical response of the system. Robust bacterial biofilms produce a plethora of molecules that promote communication, defend the colony, and cause infection. (M. B. Miller and B. L. Bassler, Annu Rev Microbiol, 2001, 55, 165-199. M. D. P. Willcox, H. Zhu, T. C. R. Conibear, E. B. H. Hume, M. Givskov, S. Kjelleberg and S. A. Rice, Microbiology, 2008, 154, 2184-2194. G. W. Lau, D. J. Hassett, H. Ran and F. Kong, Trends Mol Med, 2004, 10, 599-606.) Of interest are molecules that provide information about the condition of the biofilm, which can be detected by electrochemical methods.

SUMMARY OF THE INVENTION

The invention relates to electrochemical methods and devices that offer a simple and inexpensive alternative for immediate identification of bacterial infection due to the presence of *Pseudomonas aeruginosa*. In some embodiments, an inexpensive, disposable electrochemical sensor can be used to rapidly screen for the presence of *P. aeruginosa* in clinical wound effluent samples. This technology can be incorporated in a rapid, point-of-care diagnostic for *P.*

*aeruginosa*, allowing for better antimicrobial stewardship and improved patient care outcomes.

Other aspects of the methods and devices include the following:

1. A method of monitoring viability of a biofilm comprising *Pseudomonas aeruginosa* bacteria in a patient, the method comprising:
   (a) introducing a fluid sample from the patient into a microfluidic device including a working electrode and a reference electrode;
   (b) performing an electrochemical measurement to detect pyocyanin in the fluid sample; and
   (c) determining a concentration of pyocyanin in the fluid sample by using a previously determined correlation between pyocyanin concentration and current flow through the working electrode;
   wherein the pyocyanin concentration is the fluid sample provides a measure of the viability of the biofilm.

2. The method of item 1, further comprising estimating a number of viable cells of *Pseudomonas aeruginosa* in the biofilm based on the concentration of pyocyanin determined in step (c).

3. The method of any of items 1-2, wherein the concentration of pyocyanin is determined in step (c) based on a linear relationship of the current flow through the working electrode.

4. The method of item 3, wherein the concentration in $\mu M$ of pyocyanin is equal to the current flow in $\mu A$ through the working electrode divided by 0.18.

5. The method of any of items 1-4, wherein if the current flow through the working electrode is less than 1 $\mu A$, the pyocyanin concentration is considered to be zero.

6. The method of any of items 1-5, wherein if the current flow through the working electrode is less than 1 $\mu A$, the biofilm is considered nonviable or absent.

7. The method of any of items 1-6, wherein the electrochemical measurement is selected from the group consisting of squarewave voltammetry, linear sweep voltammetry, staircase voltammetry, cyclic voltammetry, normal pulse voltammetry, differential pulse voltammetry, and chronoamperometry.

8. The method of item 7, wherein the electrochemical measurement is square wave voltammetry and the current flow is measured in response to one or more square wave potentials.

9. The method of any of items 1-8, wherein:
   the microfluidic device comprises a second working electrode;
   the working electrode is one of an oxidizing electrode and a reducing electrode, and the second working electrode is the other of the oxidizing electrode and the reducing electrode; and
   the concentration of pyocyanin is measured as current flow through the oxidizing electrode and the reducing electrode.

10. The method of item 9, further comprising applying a potential suitable for oxidizing the pyocyanin at the oxidizing electrode and a potential suitable for reducing the pyocyanin at the reducing electrode.

11. The method of items 9-10, wherein the oxidizing electrode and the reducing electrode are separated by a distance of about 200 to 100 nm.

12. The method of any of items 1-11, wherein 10 $\mu L$ or less of the fluid sample volume is introduced.

13. The method of any of items 1-12, further comprising in step (a), continuously introducing the fluid sample into the microfluidic device.

14. The method of any of items 1-12, further comprising repeating steps (a), (b), and (c).

15. The method of item 14, wherein steps (a), (b), and (c) are repeated at least every 6 hours.

16. The method of any of items 1-15, wherein a capillary or wicking material is disposed at or near an inlet of the microfluidic device to draw the fluid sample into the device.

17. The method of any of items 1-16, wherein the microfluidic device is in communication with a potentiostat operable to control voltage at the working electrode and the reference electrode.

18. The method of item 17, wherein the microfluidic device is connectable to the potentiostat by a cable.

19. The method of any of items 1-18, wherein the microfluidic device is disposable.

20. The method of any of items 1-19, wherein the microfluidic device is worn by the patient or implanted in the patient.

21. The method of any of items 1-20, wherein the microfluidic device is embedded in a wound dressing or within or adjacent to an absorbent pad for a wound dressing.

22. The method of any of items 1-19, wherein the microfluidic device is present in a wound dressing, a bandage, a surgical implant, a catheter, a ventilator mask, a face mask, a surgical mask, or an intubation tube.

23. The method of any of items 1-19, wherein the microfluidic device is present in a contact lens case, a urine collection cup, or a urine bag.

24. The method of any of items 1-23, wherein the microfluidic device is in wireless communication with a remote monitoring station.

25. The method of any of items 1-24, wherein the fluid sample is from a human with cystic fibrosis, ventilator-associated pneumonia, a chronic wound, a burn wound, a surgical implant, or a surgical site.

26. The method of any of items 1-25, wherein the fluid sample is a bodily fluid selected from the group consisting of wound exudate, bronchial lavage, sputum, urine, saliva, spinal fluid, tears, and blood.

27. A method of monitoring effectiveness of an antibiotic treatment of a *Pseudomonas aeruginosa* infection in a patient, the method comprising:
   (a) introducing a fluid sample from the patient into a microfluidic device including a working electrode and a reference electrode;
   (b) performing an electrochemical measurement to detect pyocyanin in the fluid sample; and
   (c) determining a concentration of pyocyanin in the fluid sample by using a previously determined correlation between known concentrations of the pyocyanin and a current flow through the working electrode;
   wherein the pyocyanin concentration in the fluid sample provides a measure of the effectiveness of the antibiotic treatment.

28. The method of item 27, further comprising administering an increased dose of the antibiotic if the concentration of the pyocyanin is above a threshold level.

29. The method of item 28, wherein the threshold level of pyocyanin is a concentration of at least 5 $\mu M$.

30. The method of item 27, further comprising administering an increased dose of the antibiotic if the concentration of the pyocyanin does not drop below a threshold level after a predetermined time interval.

31. The method of item 30, wherein the predetermined time interval is at least 12 hours.

32. The method of items 30-31, wherein the threshold level of pyocyanin is a concentration of at least 5 µM.
33. The method of item 27, further comprising administering a decreased dose of the antibiotic or stopping the antibiotic if the concentration of the pyocyanin drops below a threshold level.
34. The method of item 33, wherein the threshold level of pyocyanin is a concentration of at least 5 µM.
35. The method of any of items 27-34, wherein the antibiotic is colistin sulfate or ciprofloxacin.
36. The method of any of items 27-35 further comprising administering an additional antibiotic or other pharmaceutical agent.
37. The method of any of items 27-36, wherein in step (b), continuously introducing a fluid sample into the microfluidic device.
38. The method of any of items 27-36, further comprising repeating step (b) and step (c) interval.
39. The method of item 38, wherein steps (b) and (c) are repeated at least every 6 hours.
40. The method of any of items 27-39, wherein the electrochemical measurement is selected from the group consisting of squarewave voltammetry, linear sweep voltammetry, staircase voltammetry, cyclic voltammetry, normal pulse voltammetry, differential pulse voltammetry, and chronoamperometry.
41. The method of item 40, wherein the current flow is measured in response to one or more square wave potentials.
42. The method of any of items 27-41, wherein:
    the microfluidic device comprises a second working electrode;
    the working electrode is one of an oxidizing electrode and a reducing electrode, and the second working electrode is the other of the oxidizing electrode and the reducing electrode; and
    the concentration of pyocyanin is measured as current flow through the oxidizing electrode and the reducing electrode.
43. The method of item 42, further comprising applying a potential suitable for oxidizing the pyocyanin at the oxidizing electrode and a potential suitable for reducing the pyocyanin at the reducing electrode.
44. The method of any of items 42-43, wherein the oxidizing electrode and the reducing electrode are separated by a distance of about 200 to 100 nm.
45. The method of any of items 27-44, wherein a capillary or wicking material is disposed at or near an inlet to the microfluidic device to draw the fluid sample into the microfluidic device.
46. The method of any of items 27-45, wherein the device is in communication with a potentiostat operable to control voltage at the working electrode and the reference electrode.
47. The method of item 46, wherein the microfluidic device is connectable to the potentiostat by a cable.
48. The method of any of items 27-47, wherein the microfluidic device is disposable.
49. The method of any of items 27-48, wherein the microfluidic device is worn by the patient or implanted in the patient.
50. The method of any of items 27-49, wherein the microfluidic device is embedded in a wound dressing or within or adjacent to an absorbent pad for a wound dressing.
51. The method of any of items 27-49, wherein the microfluidic device is present in a wound dressing, a surgical implant, a catheter, a ventilator mask, or an intubation tube.
52. The method of any of items 27-48, wherein the microfluidic device is present in a contact lens case, a urine collection cup, or a urine bag.
53. The method of any of items 27-52, wherein the microfluidic device is in wireless communication with a remote monitoring station.
54. The method of any of items 27-53, wherein the fluid sample is from a human with cystic fibrosis, ventilator-associated pneumonia, a chronic wound, a burn wound, a surgical implant, or a surgical site.
55. The method of any of items 27-54, wherein the fluid sample is a bodily fluid selected from the group consisting of wound exudate, bronchial lavage, sputum, urine, saliva, spinal fluid, tears, and blood.
56. A method of screening effectiveness of an antibiotic against a biofilm comprising *Pseudomonas aeruginosa*, the method comprising:
    (a) introducing a sample comprising *Pseudomonas aeruginosa* into a growth chamber in a microfluidic device including a working electrode and a reference electrode;
    (b) allowing the *Pseudomonas aeruginosa* to grow and form a biofilm in the growth chamber;
    (c) introducing an antibiotic at a selected concentration into the growth chamber of the device;
    (d) performing an electrochemical measurement to detect pyocyanin in the fluid sample;
    (e) determining a concentration of pyocyanin in the sample by using a previously determined correlation between known concentrations of the pyocyanin and a current flow through the working electrode, wherein the concentration of pyocyanin below a threshold indicates effectiveness of the antibiotic.
57. The method of item 56, wherein the threshold level comprises a concentration of at least 5 µM.
58. The method of items 56-57, further comprising providing an indication of a presence of *Pseudomonas aeruginosa* when the concentration of pyocyanin is above the threshold level, the threshold level comprising a concentration of at least 5 µM.
59. The method of any of items 56-58, further comprising estimating a number of cells of *Pseudomonas aeruginosa* based on the concentration of pyocyanin.
60. The method of any of items 56-59, wherein step (a) comprises introducing the sample comprising *Pseudomonas aeruginosa* into a plurality of growth chambers in the microfluidic device; and step (c) comprises simultaneously introducing the antibiotic at selected different concentrations into each growth chamber to screen the effectiveness of multiple concentrations of the antibiotic.
61. The method of any of items 56-60, further comprising repeating steps (a) through (c) with a different concentration of the antibiotic.
62. The method of any of items 56-60, further comprising in step (b), continuously introducing the antibiotic into the growth chamber.
63. The method of any of items 56-62, wherein the electrochemical measurement is selected from the group consisting of squarewave voltammetry, linear sweep voltammetry, staircase voltammetry, cyclic voltammetry, normal pulse voltammetry, differential pulse voltammetry, and chronoamperometry.

64. The method of item 63, wherein the current flow is measured in response to one or more square wave potentials.

65. The method of any of items 56-62, wherein:
   the microfluidic device comprises a second working electrode;
   the working electrode comprises one of an oxidizing electrode and a reducing electrode, and the second working electrode comprises the other of the oxidizing electrode and the reducing electrode; and
   the concentration of pyocyanin is measured as current flow through the oxidizing electrode and the reducing electrode.

66. The method of item 65, further comprising applying a potential suitable for oxidizing the pyocyanin at the oxidizing electrode and a potential suitable for reducing the pyocyanin at the reducing electrode.

67. The method of items 65-66, wherein the oxidizing electrode and the reducing electrode are separated by a distance of about 200 to 100 nm.

68. The method of any of items 56-67, wherein a capillary or wicking material is disposed at or near an inlet of the microfluidic device to draw the fluid sample into the device.

69. The method of any of items 56-68, wherein the microfluidic device is in communication with a potentiostat operable to control voltage at the working electrode and the reference electrode.

70. The method of item 69, wherein the microfluidic device is connectable to the potentiostat by a cable.

71. The method of any of items 56-70, wherein the microfluidic device is disposable.

72. A method of monitoring viability of a biofilm comprising *Pseudomonas aeruginosa* bacteria, the method comprising:
   (a) introducing a fluid sample into a microfluidic device including a working electrode and a reference electrode;
   (b) performing an electrochemical measurement to detect pyocyanin in the fluid sample; and
   (c) determining a concentration of pyocyanin in the fluid sample by using a previously determined correlation between pyocyanin concentration and current flow through the working electrode;
   wherein the pyocyanin concentration is the fluid sample provides a measure of the viability of the biofilm.

73. The method of item 72, wherein the microfluidic device is disposed in a contact lens case, a urine bag, a urine collection cup, a medication pump, a water pipe, a bioreactor, or a water pump.

74. The method of items 72-73, wherein the electrochemical measurement is selected from the group consisting of squarewave voltammetry, linear sweep voltammetry, staircase voltammetry, cyclic voltammetry, normal pulse voltammetry, differential pulse voltammetry, and chronoamperometry.

75. The method of item 74, wherein the electrochemical measurement is square wave voltammetry and the current flow is measured in response to one or more square wave potentials.

76. The method of any of items 72-75, wherein:
   the microfluidic device comprises a second working electrode;
   the working electrode is one of an oxidizing electrode and a reducing electrode, and the second working electrode is the other of the oxidizing electrode and the reducing electrode; and
   the concentration of pyocyanin is measured as current flow through the oxidizing electrode and the reducing electrode.

77. The method of item 76, further comprising applying a potential suitable for oxidizing the pyocyanin at the oxidizing electrode and a potential suitable for reducing the pyocyanin at the reducing electrode.

78. The method of items 76-77, wherein the oxidizing electrode and the reducing electrode are separated by a distance of about 200 to 100 nm.

79. The method of any of items 72-78, wherein a capillary or wicking material is disposed at or near an inlet of the microfluidic device to draw the fluid sample into the device.

80. The method of any of items 72-79, wherein the microfluidic device is in communication with a potentiostat operable to control voltage at the working electrode and the reference electrode.

81. The method of item 80, wherein the microfluidic device is connectable to the potentiostat by a cable.

82. The method of items 76-81, wherein the microfluidic device is disposable.

83. A device for monitoring viability of a biofilm comprising *Pseudomonas aeruginosa*, the device comprising:
   a sensor comprising a microfluidic or nanofluidic electrode assembly comprising a microfluidic or nanofluidic channel disposed in a substrate, a working electrode disposed in the microfluidic or nanofluidic channel, and a reference electrode disposed in the microfluidic or nanofluidic channel;
   a control system comprising a processor and memory, machine-readable instructions stored in the memory that, upon execution by the processor, control voltage at the working electrode and the reference electrode, and determine a concentration of pyocyanin in a fluid sample in the microfluidic or nanofluidic channel by using a previously determined correlation between known concentrations of pyocyanin and current flow through the working electrode.

84. The device of item 83, wherein the device is operable to provide an indication of the concentration of pyocyanin over a range from about 5 µM to about 1 mM.

85. The device of item 84, wherein the device is operable to provide an indication of the concentration of pyocyanin over a range from about 5 µM to a solubility limit of the pyocyanin 86. The device of any of items 83-85, wherein the controller is operable to provide an indication of a presence of *Pseudomonas aeruginosa* when the concentration of pyocyanin is above a threshold level of about 5 µM.

87. The device of any of items 83-86, wherein the controller is operable to determine a number of cells of *Pseudomonas aeruginosa* in the biofilm based on the determined concentration of pyocyanin.

88. The device of any of items 83-87, wherein the concentration of pyocyanin is determined from a linear relationship, stored in the memory, of the current flow through the working electrode.

89. The device of item 88, wherein the concentration of pyocyanin in µM is equal to the current flow in µA through the working electrode divided by 0.18.

90. The device of any of items 83-89, wherein the control system further comprises a potentiostat in communication with the processor and the sensor, the potentiostat operable to control the voltage at the working electrode and the reference electrode.

91. The device of item 90, wherein the potentiostat is in communication with the processor via a hardwired connection, via a removable cable, or via a wireless connection.
92. The device of item 91, wherein the potentiostat is battery powered.
93. The device of any of items 83-92, wherein the sensor is disposable and is connectable to the potentiostat by a cable.
94. The device of any of items 83-93, wherein the controller is operable to perform an electrochemical measurement selected from the group consisting of squarewave voltammetry, linear sweep voltammetry, staircase voltammetry, cyclic voltammetry, normal pulse voltammetry, differential pulse voltammetry, and chronoamperometry.
95. The device of item 94, wherein the current flow is measured in response to one or more square wave potentials.
96. The device of any of items 83-95, further comprising a display in communication with the controller, the display operable to display one or more of the determined concentration of pyocyanin, an indication of a presence of Pseudomonas aeruginosa, and an indication of a number of cells of Pseudomonas aeruginosa.
97. The device of any of items 83-96, wherein the sensor is embedded in a wound dressing or within or adjacent to an absorbent pad for a wound dressing.
98. The device of any of items 83-96, wherein the sensor is present in a wound dressing, a surgical implant, a catheter, a ventilator mast, an intubation tube, or a contact lens case.
99. The device of any of items 83-99, wherein the controller further includes a telecommunications network connection.

DESCRIPTION OF THE DRAWINGS

The invention will be more fully understood from the following detailed description taken in conjunction with the accompanying drawings in which.

22 h, D) 35 h, E) 40 h, and F) 45 h. Flow of 4 mg/L colistin sulfate in fresh TSB at 100 nL/min was initiated at 22 h. SWVs performed from −0.5 to 0.2 V at a frequency of 15 Hz and an amplitude voltage of 50 mV.

Figure 18:
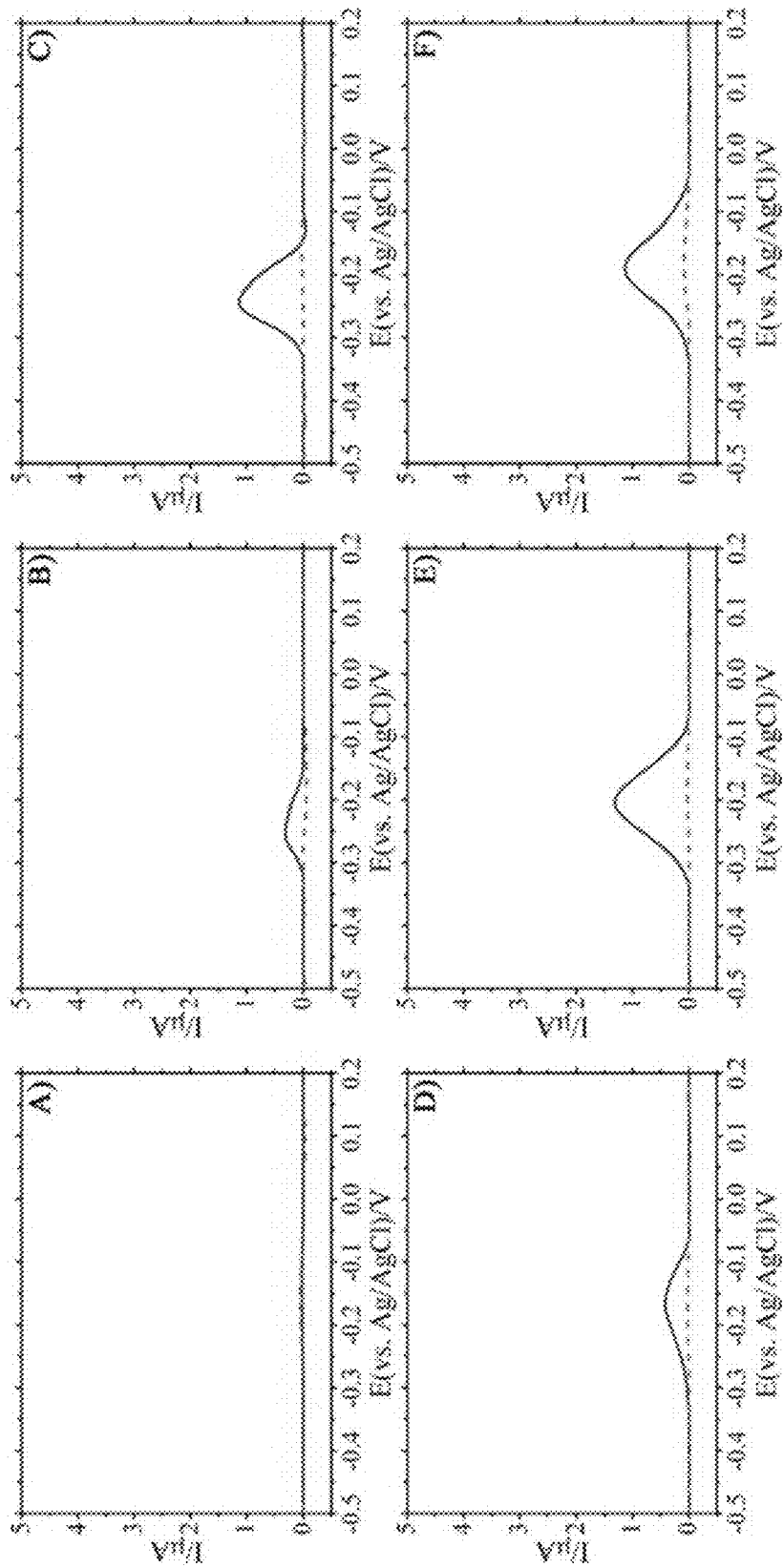

FIG. 18 illustrates SWVs of PA14 (solid lines) and *E. coli* (dashed lines) cultured in trypticase soy broth (TSB) after loading 24 μL of overnight culture after A) 0 h, B) 12 h, C) 22 h, D) 35 h, E) 40 h, and F) 45 h. Flow of 16 mg/L colistin sulfate in fresh TSB at 100 nL/min was initiated at 22 h. SWVs performed from −0.5 to 0.2 V at a frequency of 15 Hz and an amplitude voltage of 50 mV.

Figure 19:
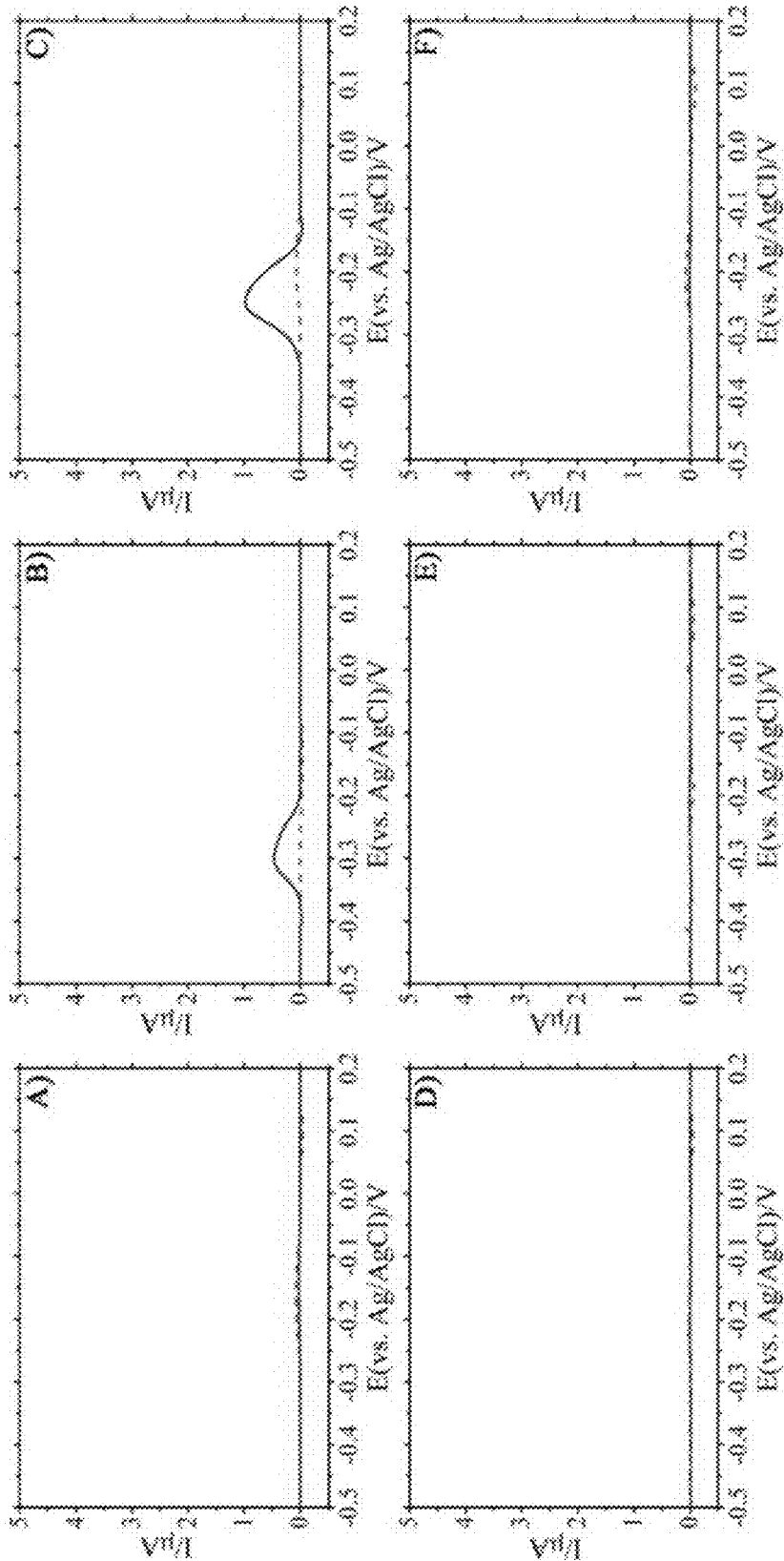

FIG. 19 illustrates SWVs of PA14 (solid lines) and *E. coli* (dashed lines) cultured in trypticase soy broth (TSB) after loading 24 μL of overnight culture after A) 0 h, B) 12 h, C) 22 h, D) 35 h, E) 40 h, and F) 45 h. Flow of 100 mg/L colistin sulfate in fresh TSB at 100 nL/min was initiated at 22 h. SWVs performed from −0.5 to 0.2 V at a frequency of 15 Hz and an amplitude voltage of 50 mV.

Figure 20:
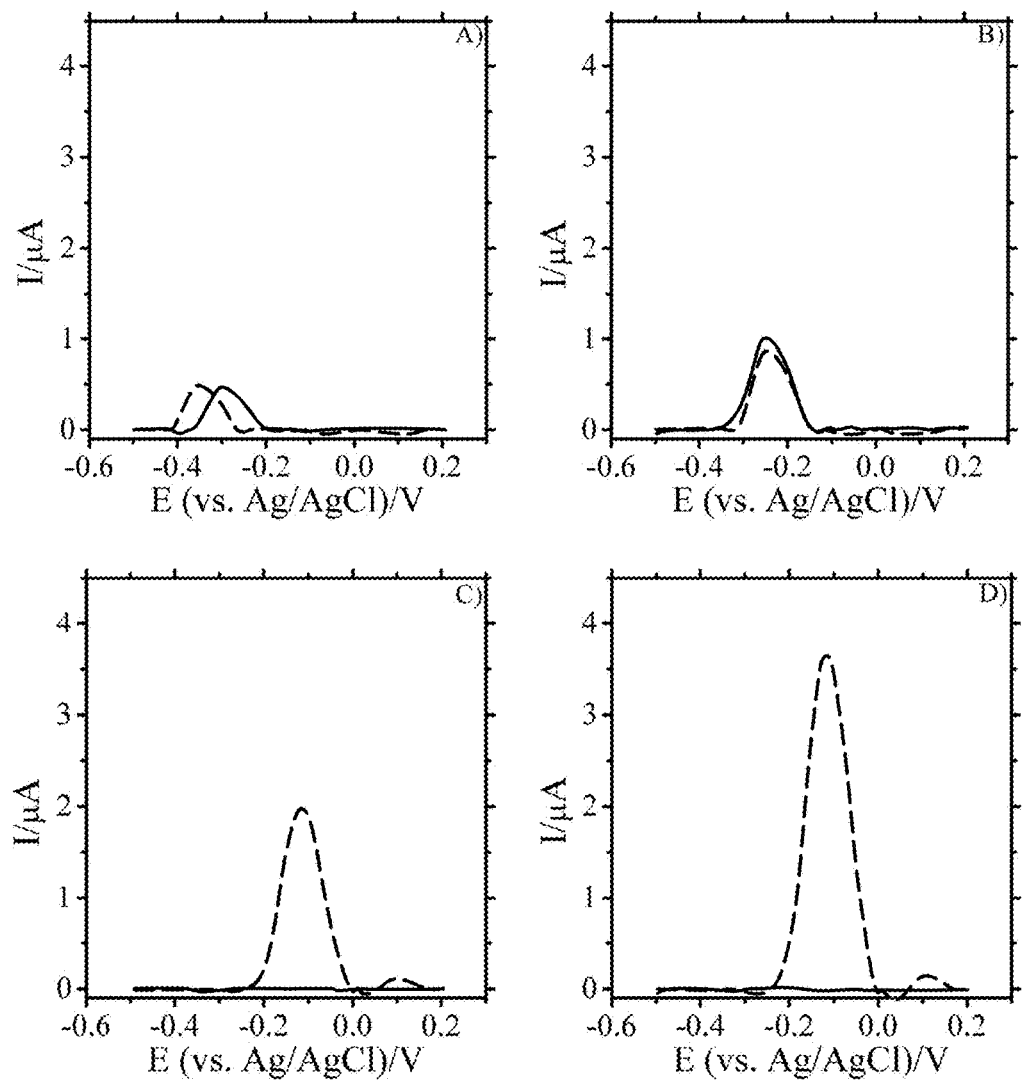

FIG. 20 illustrates SWVs of *P. aeruginosa* grown in TSB without flow for A) 12 h. The cells were then exposed to flowing 100 mg/L ampicillin (light lines) or colistin sulfate (dark lines) in TSB starting at B) 22 h. SWVs C) 35 h and D) 40 h after the start of the experiment. Baseline signal was subtracted from resulting scans. SWV performed from −0.5 to 0.2 volts at a frequency of 15 Hz and an amplitude voltage of 50 mV.

Figure 21:
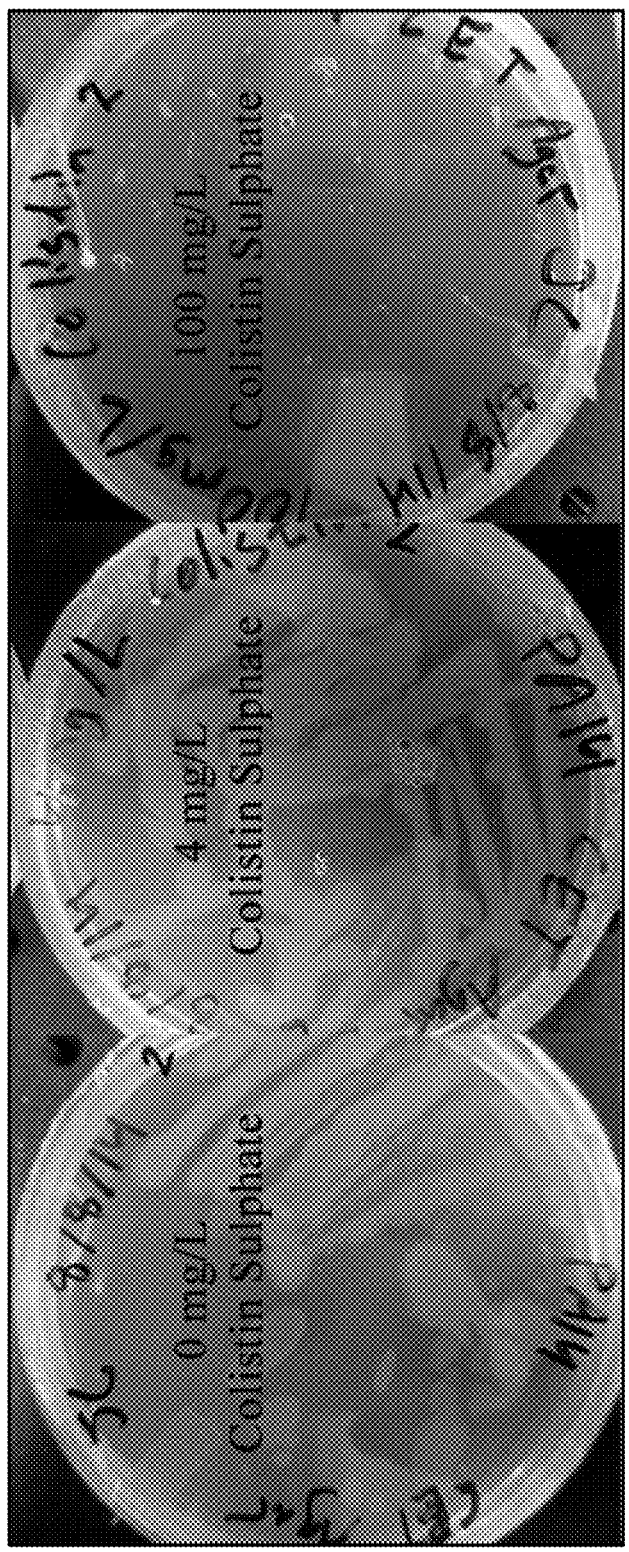

FIG. 21 illustrates images of PA14 colonies after 20 hours of growth at 37° C. on cetrimide agar plates mixed with different concentrations of colistin sulfate.

Figure 22:
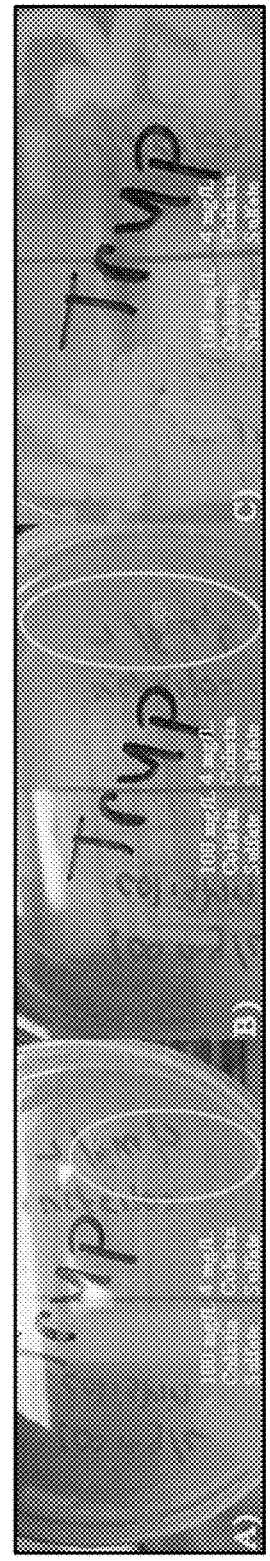

FIG. 22 illustrates PA14 streaked onto TSB after exposure to 100 mg/L and 4 mg/L colistin for 20 hours within PDMS flow chambers. Photographs show the plate after A) 4.33 h, B) 6.5 h, and C) 74.3 h of incubation. The plate was incubated at 37° C. for the first 24 hours, then grown at room temperature for the remaining time to prevent the agar from drying out.

Figure 23:
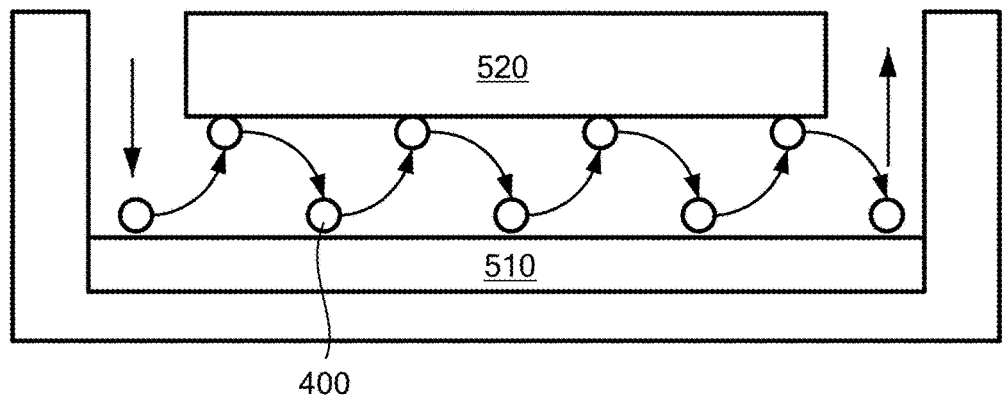

FIG. 23 is a schematic illustration of one embodiment of a sensor for monitoring viability of a biofilm comprising *Pseudomonas aeruginosa* and performing other methods as described herein.

Figure 24:
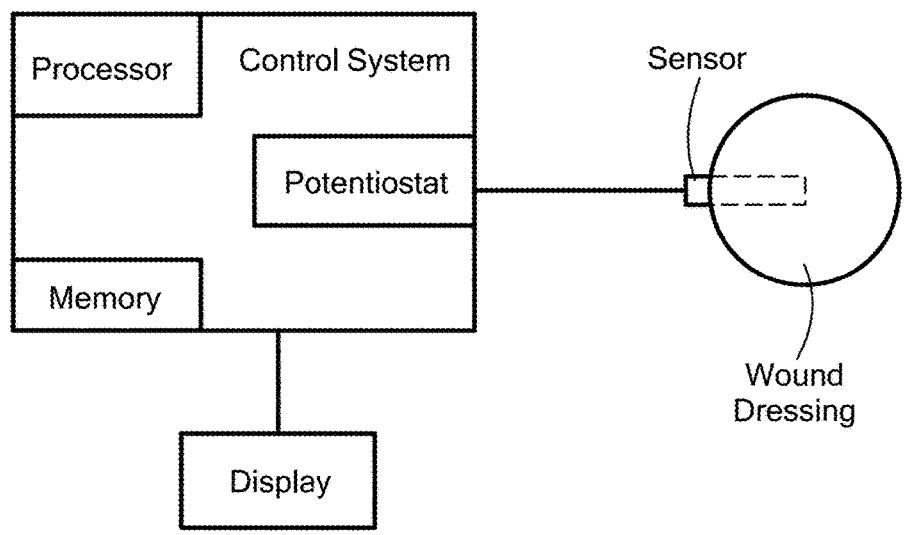

FIG. 24 is a schematic illustration of an embodiment of a device for monitoring viability of a biofilm comprising *Pseudomonas aeruginosa*.

DETAILED DESCRIPTION OF THE INVENTION

This application incorporates by reference the entire disclosure of U.S. Provisional Application No. 62/051,099 filed on Sep. 16, 2014, entitled "Diagnostic System and Process for Rapid Bacterial Infection Diagnosis", and the entire disclosure of U.S. Provisional Application No. 62/215,379 filed on Sep. 8, 2015, entitled "Diagnostic System and Process for Rapid Bacterial Infection Diagnosis".

The present invention relates to using an inexpensive, disposable electrochemical sensor for the rapid identification of *Pseudomonas aeruginosa* in clinical patient samples. The presence of *P. aeruginosa* can be electrochemically determined by its production of pyocyanin (PYO), a unique, redox-active chemical marker. In some embodiments, a simple, electrochemical detection strategy is provided that requires no sample preparation, takes less than a minute to operate, and requires only 7.5 microliters of sample to complete the analysis.

Electrochemically monitoring the viability of *P. aeruginosa* cells in a microfluidic system has previously been demonstrated. (L. Pires, K. Sachsenheimer, T. Kleintschek, A. Waldbaur, T. Schwartz and B. E. Rapp, *Biosens Bioelectron*, 2013, 47, 157-163.) Pires et al. (2013) combined impedance and amperometric measurements to simultaneously monitor the growth and respiration of *P. aeruginosa* cells. This approach emphasizes the potential to non-destructively observe *P. aeruginosa*, but it lacks the ability to measure the produced PYO itself, a potential marker of cell viability and virulence. (X. Mulet, G. Cabot, A. A. Ocampo-Sosa, M. A. Domínguez, L. Zamorano, C. Juan, F. Tubau, C. Rodríguez, B. Moyà, C. Peña, L. Martínez-Martínez and A. Oliver, *Antimicrob Agents Chemother*, 2013, 57, 5527-5535.)

One way of measuring excreted PYO electrochemically is accomplished by square wave voltammetry (SWV) over the range of voltages where PYO is reduced (half wave potential is approximately −250 mV vs. Ag/AgCl reference) via the following reaction:

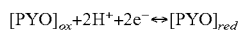

$$[PYO]_{ox} + 2H^+ + 2e^- \leftrightarrow [PYO]_{red}$$

(T. A. Webster and E. D. Goluch, *Lab Chip*, 2012, 12, 5195-5201.) The ability to measure a virulence factor as it relates to the amount of live cells in a biofilm during exposure to antibiotics, could help in determining effective treatment procedures.

As used herein, a microfluidic device can include a nanofluidic device. Also as used herein, the term "nanoscale" refers to an object or a feature whose size is in the range from about 1 nm to about 999 nm, or to less than 1 μm. The term "microscale" refers to an object of feature whose size is in the range from about 1 μm to about 999 μm, or to less than 1 mm. A nanofluidic device as used herein is a device having at least one dimension, such as a channel diameter, of nanoscale size. A microfluidic device as used herein is a device having at least one dimension, such as a channel diameter or channel length, in the microscale range.

In some embodiments, methods are provided of monitoring viability of a biofilm comprising *Pseudomonas aeruginosa* bacteria based on the detection of pyocyanin. In some embodiments, a method of monitoring viability of a biofilm comprising *Pseudomonas aeruginosa* bacteria in a patient includes the steps of (a) introducing a fluid sample from the patient into a microfluidic device including a working electrode and a reference electrode; (b) performing an electrochemical measurement to detect pyocyanin in the fluid sample; and (c) determining a concentration of pyocyanin in the fluid sample by using a previously determined correlation between pyocyanin concentration and current flow through the working electrode. The pyocyanin concentration is the fluid sample provides a measure of the viability of the biofilm.

More particularly, a fluid sample from a patient in introduced into a microfluidic device including a working electrode and a reference electrode. Suitable microfluidic devices are described in WO/2014/015333 and WO/2015/031798, the disclosures of which are incorporated by reference herein. An electrochemical measurement is performed to detect pyocyanin in the fluid sample, and a concentration of pyocyanin in the fluid sample is determined by using a previously determined correlation between pyocyanin concentration and current flow through the working electrode. The pyocyanin concentration is the fluid sample provides a measure of the viability of the biofilm. The concentration of pyocyanin can be determined based on a linear relationship of the current flow through the working electrode. See, for example, FIG. 13, described further below. In some embodiments, the concentration in μM of pyocyanin is equal to the current flow in μA through the working electrode divided by 0.18. In other embodiments, the current flow in µA through the working electrode divided by 0.10, 0.14, 0.16, 0.20, 0.22, or 0.26. In some embodiments, if the current flow through the working electrode is less than 1 µA, the pyocyanin concentration is considered to be zero.

In some embodiments, if the current flow through the working electrode is less than 1 µA, the biofilm is considered nonviable or absent. In some embodiments, a number of viable cells of *Pseudomonas aeruginosa* in the biofilm can be estimated based on the determined concentration of pyocyanin. (T. A. Webster, H. J. Sismaet, A. F. Sattler, E. D. Goluch, Improved monitoring of *P. aeruginosa* on agar plates, *Anal. Methods*, 2015, 7, 7150-7155.)

The electrochemical measurement can be made in any suitable manner. For example, the electrochemical measurement can be made by squarewave voltammetry, linear sweep voltammetry, staircase voltammetry, cyclic voltammetry, normal pulse voltammetry, differential pulse voltammetry, and chronoamperometry. In some embodiments, the electrochemical measurement is square wave voltammetry and the current flow is measured in response to one or more square wave potentials.

In some embodiments, the microfluidic device can include an oxidizing electrode and a reducing electrode (the working electrodes). The concentration of pyocyanin is measured as current flow through the oxidizing electrode and the reducing electrode. A potential suitable for oxidizing the pyocyanin is applied at the oxidizing electrode and a potential suitable for reducing the pyocyanin is applied at the reducing electrode.

The working electrodes can make up a wall or part of a wall of a channel, such as a microfluidic channel or a nanofluidic channel, into which the fluid sample is introduced and within which the redox reaction takes place. In some embodiments, the oxidizing electrode and the reducing electrode are separated by a distance of about 200 to 100 nm. In other embodiments, the distance can be from about 20 nm to about 100 nm, or from about 20 nm to about 40 nm, or from about 40 nm to about 60 nm, or from about 60 nm to about 80 nm, or from about 80 nm to about 100 nm, or from about 100 nm to about 150 nm.

The surface area of the working electrodes can be selected to accommodate a desired size of the device. A larger surface area generally improves the signal and sensitivity of the device. For example, in different embodiments, the surface area of each working electrode can be about 100, 200, 300, 400, 500, 800, 1000, 200, 3000, 5000, 10000, 50000, 100000, 200000, or 500000 $nm^2$, or 1, 2, 5, 10 $\mu m^2$, or greater.

In other embodiments, the fluid sample can be introduced into a well, chamber, or another form of receptacle in which the reaction can take place. The volume of the channel, well, chamber or other receptacle can be less than about 50 nanoliters (nL), less than about 10 nL, less than about 1 nL, less than about 100 picoliters (pL), less than about 50 pL, less than about 10 pL, less than about 5 pL, or less than about 1 pL.

In some embodiments, a sample volume that is introduced into the microfluidic device can be less than 100 µL, less than 50 µL, less than 20 µL, less than 10 µL, less than 5 µL, less than 2 µL, or less than 1 µL.

In some embodiments, the fluid sample can be introduced continuously into the microfluidic device. In other embodiments, fluid samples are introduced repeated into the microfluidic device. For example, the steps of introducing a fluid sample into the device, performing an electrochemical measurement to detect pyocyanin in the fluid sample, and determining a concentration of pyocyanin in the fluid sample can be performed repeatedly at time intervals. In some embodiments, the steps can be repeated at least every 6 hours, every 12 hours, every 18 hours, every 24 hours, or every 48 hours.

In some embodiments, a capillary or wicking material can be disposed at or near an inlet of the microfluidic device to draw the fluid sample into the device. Is some embodiments, a matrix material can be disposed at or near an inlet of a microfluidic device, for example, to isolate the electrodes from the bacteria while permitting passage of pyocyanin to access the electrodes.

One exemplary embodiment of a microfluidic device is illustrated in FIG. 23. The device includes a first working electrode 510 and a second working electrode 520. Pyocyanin 400 in a channel between the electrodes undergoes a reduction-oxidation cycle at the first 510 and second 520 electrodes, indicated schematically with arrows.

In some embodiments, the microfluidic device can be in communication with a potentiostat operable to control voltage at the working electrode and the reference electrode. See FIG. 24. The microfluidic device can be connectable to the potentiostat by a cable. The microfluidic device can be in wireless communication with a remote monitoring station. The microfluidic device can be disposable, such as a disposable sensor that can be disconnected from the potentiostat to allow a fresh sensor to be used.

In some embodiments, the microfluidic device can be worn by the patient or implanted in the patient. For example, in some embodiments, the microfluidic device can be embedded in a wound dressing or within or adjacent to an absorbent pad for a wound dressing. With such embodiments, a wound can be continuously or repeatedly monitored for the presence of *Pseudomonas aeruginosa*, and upon detection of pyocyanin, an appropriate selective antibiotic can be administered to the patient.

In other embodiments, the microfluidic device can be present in a wound dressing, a bandage, a surgical implant, a catheter, a ventilator mask, a face mask, a surgical mask, or an intubation tube. In still other embodiments, the microfluidic device can be present in a contact lens case, a urine collection cup, or a urine bag.

The fluid sample can be from a human with cystic fibrosis, ventilator-associated pneumonia, a chronic wound, a burn wound, a surgical implant, or a surgical site. The fluid sample can be a bodily fluid from a wound exudate, bronchial lavage, sputum, urine, saliva, spinal fluid, tears, and blood.

In other aspects, methods of monitoring viability of a biofilm comprising *Pseudomonas aeruginosa* bacteria can be used in other applications. For example, a bioreactor for treating medical or other waste products can become contaminated with bacteria. The bacteria can be introduced through a variety of mechanisms, including through the waste products, through a water feed pipe, or through the addition of other additives used to break down waste. In some embodiments, a microfluidic device are described and used herein can be disposed in a contact lens case, a urine bag, a urine collection cup, a medication pump, a water pipe, a bioreactor, or a water pump.

In another aspect of the invention, methods of monitoring effectiveness of an antibiotic treatment of a *Pseudomonas aeruginosa* infection in a patient are provided. In some embodiments, the method includes steps of (a) introducing a fluid sample from the patient into a microfluidic device including a working electrode and a reference electrode; (b) performing an electrochemical measurement to detect pyocyanin in the fluid sample; and (c) determining a concentration of pyocyanin in the fluid sample by using a previously determined correlation between known concentrations of the pyocyanin and a current flow through the working electrode. The pyocyanin concentration in the fluid sample provides a measure of the effectiveness of the antibiotic treatment.

An increased dose of the antibiotic can be administered if the concentration of the pyocyanin is above a threshold level. In some embodiments, the threshold level of pyocyanin can be a concentration of at least 1 µM, at least 5 µM, or at least 10 µM. In some embodiments, the methods can include administering an increased dose of the antibiotic if the concentration of the pyocyanin does not drop below a threshold level after a predetermined time interval. The predetermined time interval can be at least 6 hours, at least 12 hours, at least 18 hours, at least 24 hours, at least 48 hours, or greater. In some embodiments, the methods can include administering a decreased dose of the antibiotic or stopping the antibiotic if the concentration of the pyocyanin drops below a threshold level. In some embodiments, the threshold level of pyocyanin can be a concentration of at least 1 µM, at least 5 µM, or at least 10 µM.

In some embodiments, the antibiotic can be colistin sulfate or ciprofloxacin. In other embodiments, the methods can include administering an additional antibiotic or other pharmaceutical agent.

In a further aspect of the invention, methods of screening effectiveness of an antibiotic against a biofilm comprising *Pseudomonas aeruginosa* are provided. In some embodiments, the method includes steps of (a) introducing a sample comprising *Pseudomonas aeruginosa* into a growth chamber in a microfluidic device including a working electrode and a reference electrode; (b) allowing the *Pseudomonas aeruginosa* to grow and form a biofilm in the growth chamber; (c) introducing an antibiotic at a selected concentration into the growth chamber of the device; (d) performing an electrochemical measurement to detect pyocyanin in the fluid sample; and (e) determining a concentration of pyocyanin in the sample by using a previously determined correlation between known concentrations of the pyocyanin and a current flow through the working electrode. The concentration of pyocyanin below a threshold indicates effectiveness of the antibiotic.

In some embodiments, a threshold level of pyocyanin can be a concentration below 1 µM, 5 µM, or 10 µM, 20 µM, 30 µM, 40 µM, 50 µM, 100 µM, or 200 µM.

In some embodiments, the method includes providing an indication of a presence of *Pseudomonas aeruginosa* when the concentration of pyocyanin can be above 1 µM, 5 µM, or 10 µM, or greater. In some embodiments, the method includes estimating a number of cells of *Pseudomonas aeruginosa* based on the concentration of pyocyanin.

In some embodiments, the method includes introducing a sample comprising *Pseudomonas aeruginosa* into a plurality of growth chambers in the microfluidic device; and simultaneously introducing the antibiotic at selected different concentrations into each growth chamber to screen the effectiveness of multiple concentrations of the antibiotic.

In some embodiments, the method steps can be repeated with a different concentration of the antibiotic. In some embodiments, the methods can include continuously introducing the antibiotic into a growth chamber.

A device for carrying out the methods described herein can be provided.

In some embodiments, a device for monitoring viability of a biofilm comprising *Pseudomonas aeruginosa* can include a sensor having a microfluidic (or nanofluidic) electrode assembly comprising a microfluidic (or nanofluidic) channel disposed in a substrate. A working electrode and a reference electrode can be disposed in the microfluidic channel. A control system is provided, including a processor and memory. Machine-readable instructions can be stored in the memory that, upon execution by the processor, control the voltage at the working electrode and the reference electrode, and determine a concentration of pyocyanin in a fluid sample in the microfluidic channel by using a previously determined correlation between known concentrations of pyocyanin and current flow through the working electrode.

In some embodiments, the device is operable to provide an indication of the concentration of pyocyanin over a range from about 1 µM to about 1 mM, or from about 5 µM to about 1 mM. In some embodiments, the concentration range can have a lower limit of 1 µM, 5µM or 10 µM. In some embodiments, the concentration range can have an upper limit of 50 µM, or about 1 mM. In some embodiments, the concentration range can have an upper limit of a solubility limit of pyocyanin.

In some embodiments, the control system is operable to provide an indication of a presence of *Pseudomonas aeruginosa* when the concentration of pyocyanin is above a threshold level. In some embodiments, the threshold level is about 1 µM, or about 5 µM, or about 10 µM. In some embodiments, the control system is operable to determine a number of cells of *Pseudomonas aeruginosa* in the biofilm based on the determined concentration of pyocyanin.

In some embodiments, the concentration of pyocyanin can be determined from a linear relationship, stored in the memory, of the current flow through the working electrode. In some embodiments, the concentration in µM of pyocyanin is equal to the current flow in µA through the working electrode divided by 0.18. In other embodiments, the current flow in µA through the working electrode divided by 0.10, 0.14, 0.16, 0.20, 0.22, or 0.26. In some embodiments, if the current flow through the working electrode is less than 1 µA, the pyocyanin concentration is considered to be zero.

In some embodiments, the control system includes a potentiostat in communication with the processor and the sensor. The potentiostat is operable to control the voltage at the working electrode and the reference electrode. The potentiostat can be in communication with the processor via a hardwired connection, via a removable cable, or via a wireless connection. The potentiostat can be in communication with the sensor via a cable, which can be disconnectable. The potentiostat can be is battery powered.

The control system is operable to perform an electrochemical measurement using squarewave voltammetry, linear sweep voltammetry, staircase voltammetry, cyclic voltammetry, normal pulse voltammetry, differential pulse voltammetry, and chronoamperometry. In some embodiments, the current flow is measured in response to one or more square wave potentials.

The device can also include a display in communication with the control system, which can be operable to display one or more of the determined concentration of pyocyanin, an indication of a presence of *Pseudomonas aeruginosa*, and an indication of a number of cells of *Pseudomonas aeruginosa*.

In some embodiments, the sensor can be disposable and can be connectable to the potentiostat by a cable. The sensor, particularly, a disposable sensor, can be embedded in a wound dressing or within or adjacent to an absorbent pad for a wound dressing. In some embodiments, the sensor can be present in a wound dressing, a surgical implant, a catheter, a ventilator mast, or an intubation tube. In other embodiments, the sensor can be embedded in a contact lens case, a urine bag or a urine collection cup.

The control system can include a telecommunications network connection, for example, to enable communication to a remote monitoring station.

It will be appreciated that the control system can be part of a computer system that executes programming for controlling the methods and devices as described herein. The computing system can be implemented as or can include a computing device that includes a combination of hardware, software, and firmware that allows the computing device to run an applications layer or otherwise perform various processing tasks. Computing devices can include without limitation personal computers, work stations, servers, laptop computers, tablet computers, mobile devices, hand-held devices, wireless devices, smartphones, wearable devices, embedded devices, microprocessor-based devices, microcontroller-based devices, programmable consumer electronics, mini-computers, main frame computers, and the like.

The computing device can include a basic input/output system (BIOS) and an operating system as software to manage hardware components, coordinate the interface between hardware and software, and manage basic operations such as start up. The computing device can include one or more processors and memory that cooperate with the operating system to provide basic functionality for the computing device. The operating system provides support functionality for the applications layer and other processing tasks. The computing device can include a system bus or other bus (such as memory bus, local bus, peripheral bus, and the like) for providing communication between the various hardware, software, and firmware components and with any external devices. Any type of architecture or infrastructure that allows the components to communicate and interact with each other can be used.

Processing tasks can be carried out by one or more processors. Various types of processing technology can be used, including a single processor or multiple processors, a central processing unit (CPU), multicore processors, parallel processors, or distributed processors. Additional specialized processing resources such as graphics (e.g., a graphics processing unit or GPU), video, multimedia, or mathematical processing capabilities can be provided to perform certain processing tasks. Processing tasks can be implemented with computer-executable instructions, such as application programs or other program modules, executed by the computing device. Application programs and program modules can include routines, subroutines, programs, drivers, objects, components, data structures, and the like that perform particular tasks or operate on data.

The computing device includes memory or storage, which can be accessed by the system bus or in any other manner. Memory can store control logic, instructions, and/or data. Memory can include transitory memory, such as cache memory, random access memory (RAM), static random access memory (SRAM), main memory, dynamic random access memory (DRAM), and memristor memory cells. Memory can include storage for firmware or microcode, such as programmable read only memory (PROM) and erasable programmable read only memory (EPROM). Memory can include non-transitory or nonvolatile or persistent memory such as read only memory (ROM), hard disk drives, optical storage devices, compact disc drives, flash drives, floppy disk drives, magnetic tape drives, memory chips, and memristor memory cells. Non-transitory memory can be provided on a removable storage device. A computer-readable medium can include any physical medium that is capable of encoding instructions and/or storing data that can be subsequently used by a processor to implement embodiments of the method and system described herein. Physical media can include floppy discs, optical discs, CDs, mini-CDs, DVDs, HD-DVDs, Blu-ray discs, hard drives, tape drives, flash memory, or memory chips. Any other type of tangible, non-transitory storage that can provide instructions and/or data to a processor can be used in these embodiments.

The computing device can include one or more input/output interfaces for connecting input and output devices to various other components of the computing device. Input and output devices can include, without limitation, keyboards, mice, joysticks, microphones, displays, monitors, scanners, speakers, and printers. Interfaces can include universal serial bus (USB) ports, serial ports, parallel ports, game ports, and the like.

The computing device can access a network over a network connection that provides the computing device with telecommunications capabilities. Network connection enables the computing device to communicate and interact with any combination of remote devices, remote networks, and remote entities via a communications link. The communications link can be any type of communication link, including without limitation a wired or wireless link. For example, the network connection can allow the computing device to communicate with remote devices over a network, which can be a wired and/or a wireless network, and which can include any combination of intranet, local area networks (LANs), enterprise-wide networks, medium area networks, wide area networks (WANs), the Internet, or the like. Control logic and/or data can be transmitted to and from the computing device via the network connection. The network connection can include a modem, a network interface (such as an Ethernet card), a communication port, a PCMCIA slot and card, or the like to enable transmission of and receipt of data via the communications link.

The computing device can include a browser and a display that allow a user to browse and view pages or other content served by a web server over the communications link. A web server, server, and database can be located at the same or at different locations and can be part of the same computing device, different computing devices, or distributed across a network. A data center can be located at a remote location and accessed by the computing device over a network.

The computer system can include architecture distributed over one or more networks, such as, for example, a cloud computing architecture. Cloud computing includes without limitation distributed network architectures for providing, for example, software as a service (SaaS), infrastructure as a service (IaaS), platform as a service (PaaS), network as a service (NaaS), data as a service (DaaS), database as a service (DBaaS), backend as a service (BaaS), test environment as a service (TEaaS), API as a service (APIaaS), and integration platform as a service (IPaaS).

The methods and devices described herein can be used in a variety of hospitable and other medical settings, such as post operation facilities, emergency rooms, ICUs, burn wards, central laboratories, and outpatient facilities, such as for diabetes patients.

EXAMPLE 1

In one study, the use was evaluated of an inexpensive disposable electrochemical sensor to screen wound fluid exudate sampled obtained from patients with chronic wounds for the presence of *Pseudomonas aeruginosa*.

Materials and Methods

This research was conducted through the Wound Etiology and Healing (WE-HEAL) Study, a biospecimen and data repository designed for studying chronic wounds approved by the George Washington University Institutional Review Board (041408). Subjects are eligible for this study if they have an open wound at the time of evaluation and are older than 18 years of age. All subjects gave written informed consent for collection of specimens and data.

For this experiment, 14 paired wound fluid and biofilm samples from 12 patients were selected for analysis. This was a convenience sample selected based on availability of wound fluid and wound microbiome samples from the same collection date.

According to standard operating procedures for the WE-HEAL Study, wound effluent specimens were collected using the Levine technique. (Levine, N. S., et al., *The quantitative swab culture and smear: A quick, simple method for determining the number of viable aerobic bacteria on open wounds*. J Trauma, 1976. 16(2): p. 89-94.) This technique has been well validated to ensure standardization throughout all specimens collected in the WE-HEAL Study. After collection, the swabs were immediately placed in 0.65 µm pore size centrifugal filters (Ultrafree-MC DV, Merck Millipore, Mass., USA). Samples were centrifuged at 12000 rpm for 4 minutes to extract the wound exudate and remove cellular and fibrinous debris. Samples were stored at −80° C. until analysis.

According to standard operating procedures for the WE-HEAL Study, wound biofilm specimens were collected by swabbing the wound with a cotton swab also using the Levine technique. (Levine, N. S., et al., *The quantitative swab culture and smear: A quick, simple method for determining the number of viable aerobic bacteria on open wounds*. J Trauma, 1976. 16(2): p. 89-94. Angel, D. E., et al., *The clinical efficacy of two semi-quantitative wound-swabbing techniques in identifying the causative organism(s) in infected cutaneous wounds*. Int Wound J, 2011. 8(2): p. 176-85.) Samples were then stored at −80° C. until analysis.

Bacterial DNA for 16S sequencing was isolated from biofilm samples using enzymatic lysis followed by phenolchloroform isoamyl alcohol extraction and ethanol precipitation. (Chomczynski, P. and N. Sacchi, *Single-step method of RNA isolation by acid guanidinium thiocyanate-phenolchloroform extraction*. Anal Biochem, 1987. 162(1): p. 156-9.) Utilizing established 454 FLX sequencing methods (454 Life Sciences, Roche Inc., Branford, Conn., USA), universal PCR primers with unique barcode identifiers were used to amplify the hypervariable regions of the bacterial 16S rRNA gene. Taxonomic classification was performed using mothur software (University of Michigan, USA) based on the 16S rRNA gene reference sequences from the Ribosomal Database Project. (Cole, J. R., et al., *The Ribosomal Database Project: improved alignments and new tools for rRNA analysis*. Nucleic Acids Res, 2009. 37(Database issue): p. D141-5.) Biofilm specimens were considered to be positive for *Pseudomonas* spp. if any *Pseudomonas* reads were detected in the specimen regardless of relative abundance.

Figure 1:
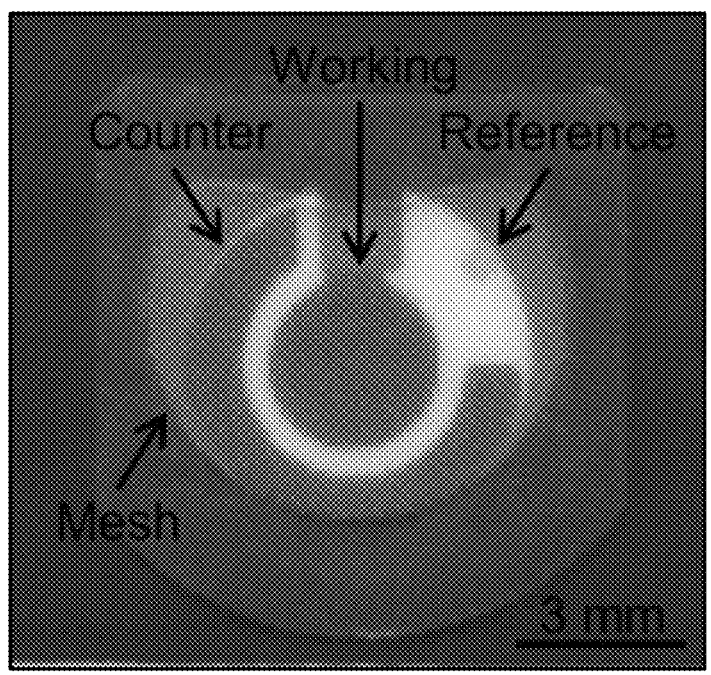
FIG. 1 illustrates a disposable, screen-printed electrode sensor with mesh modification for small-volume analysis.
Figure 2:
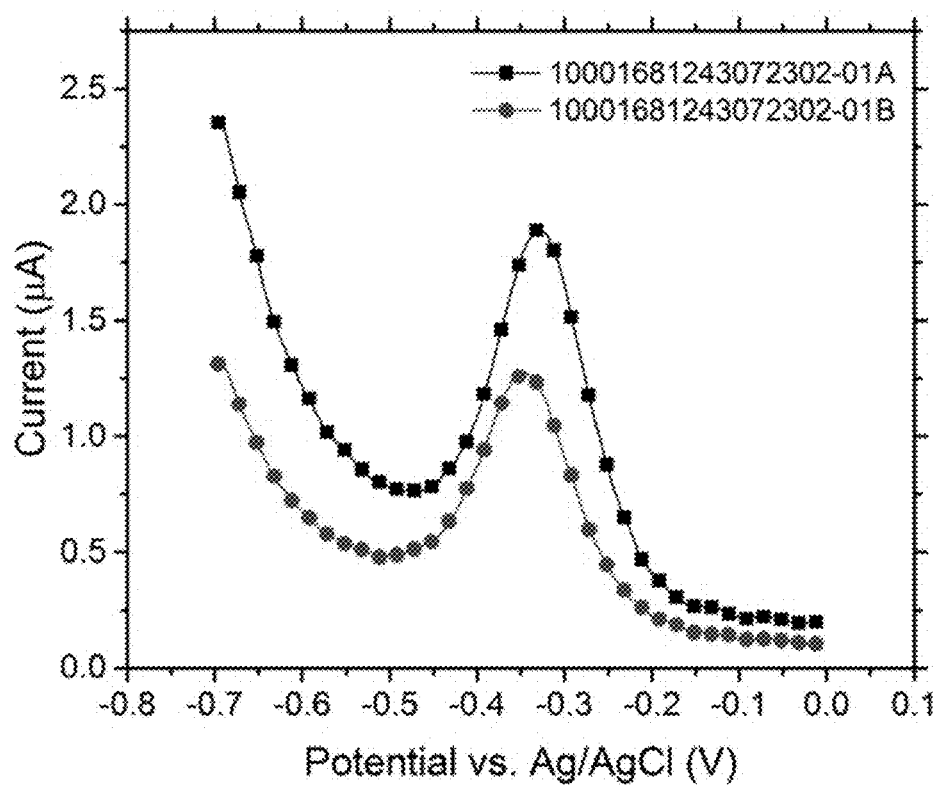
FIG. 2 is a graph of square wave voltammograms of wound fluid exudate in which a pyocyanin peak indicates the presence of Pseudomonas aeruginosa in the sample.
Figure 3:
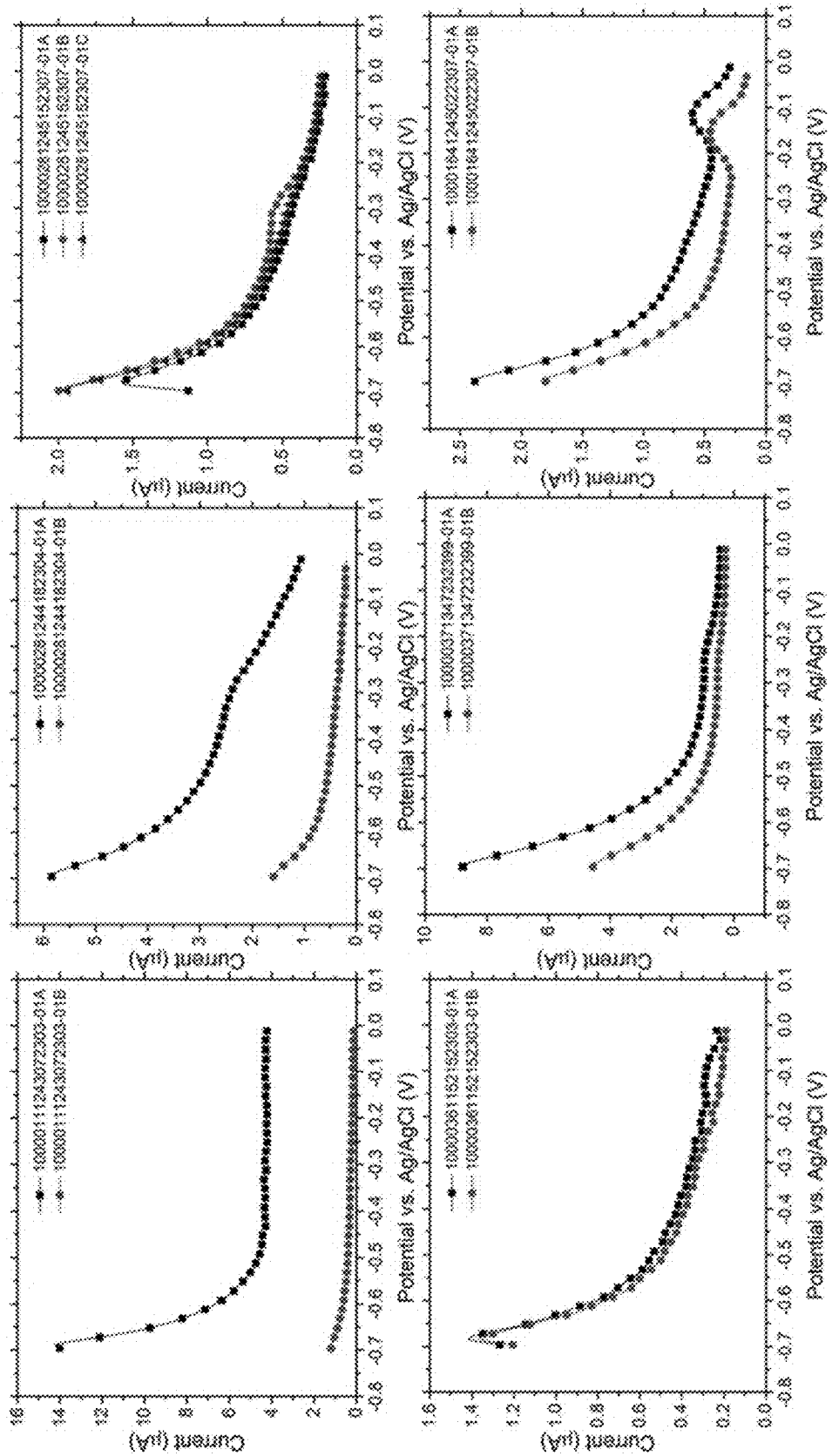
FIG. 3 illustrates a series of square wave voltammograms of wound fluid exudate.
Figure 8:
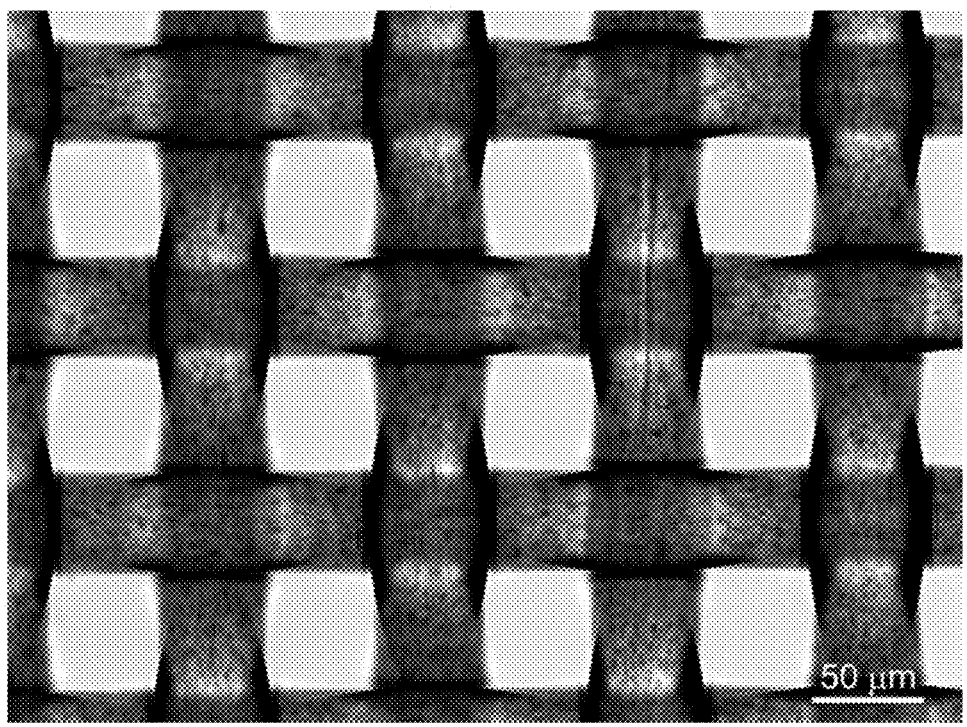
FIG. 8 is a bright-field image of a membrane mesh placed on top of an electrode sensor for small-volume analysis.

Disposable, screen-printed electrode sensors (TE100, Zensor, Taichung City, Taiwan) were used to detect the presence of pyocyanin in clinical samples (FIG. 1). The sensors utilize a 3-electrode setup, containing carbon-based working (3 mm diameter disk) and counter electrodes along with a Ag/AgCl reference electrode. FIG. 8 illustrates a bright-field image of a membrane mesh placed on top of the electrode sensor for small volume analysis. All electrochemical measurements were recorded using a portable potentiostat (µStat 200, Dropsens, Parque Tecnológico de Asturias, Spain). The sensing surface was covered with polymeric membrane (DRP-MEMB, Dropsens, Parque Tecnológico de Asturias, Spain) to reduce the amount of sample volume required for analysis.

For each test, 7.5 µA of wound exudate was pipetted into the detector well. Squarewave voltammetric scans were performed at potentials ranging from −0.7 to 0.0 V at an amplitude voltage of 0.05 V, step voltage of 0.004 V, and a frequency of 15 Hz. (See FIGS. 2-7).

Figure 4:
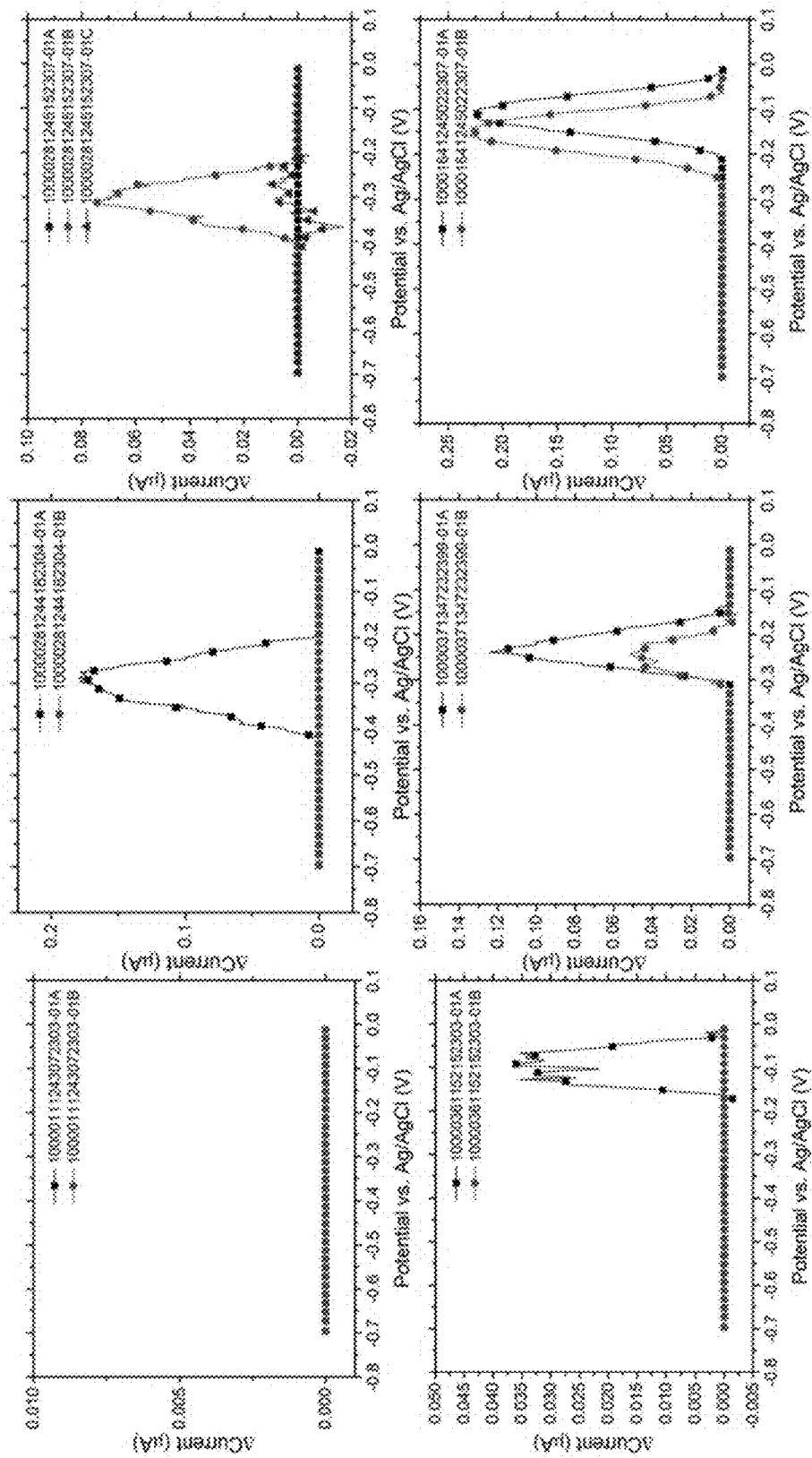
FIG. 4 illustrates baseline-subtracted square wave voltammograms of wound fluid exudate of FIG. 3.
Figure 5:
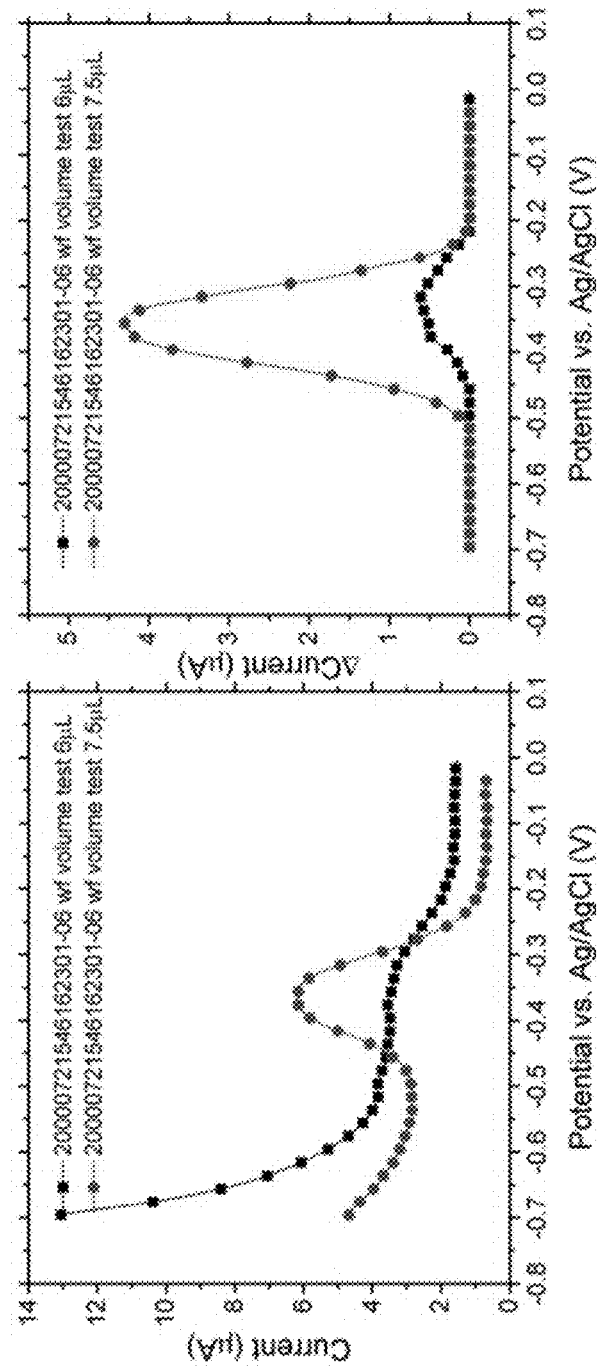
FIG. 5 illustrates square wave voltammograms of wound fluid exudate for two different volumes tested before (left) and after (right) baseline subtraction.
Figure 6:
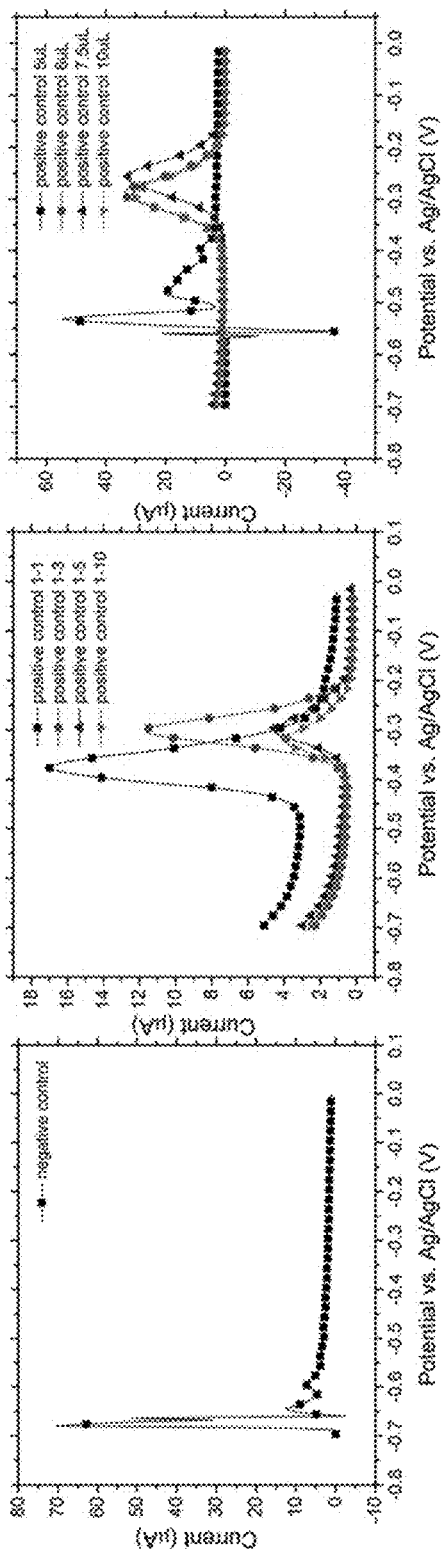
FIG. 6 illustrates square wave voltammograms of wound fluid exudate of negative control (left), positive controls (middle), and positive control at different volumes (right).
Figure 7:
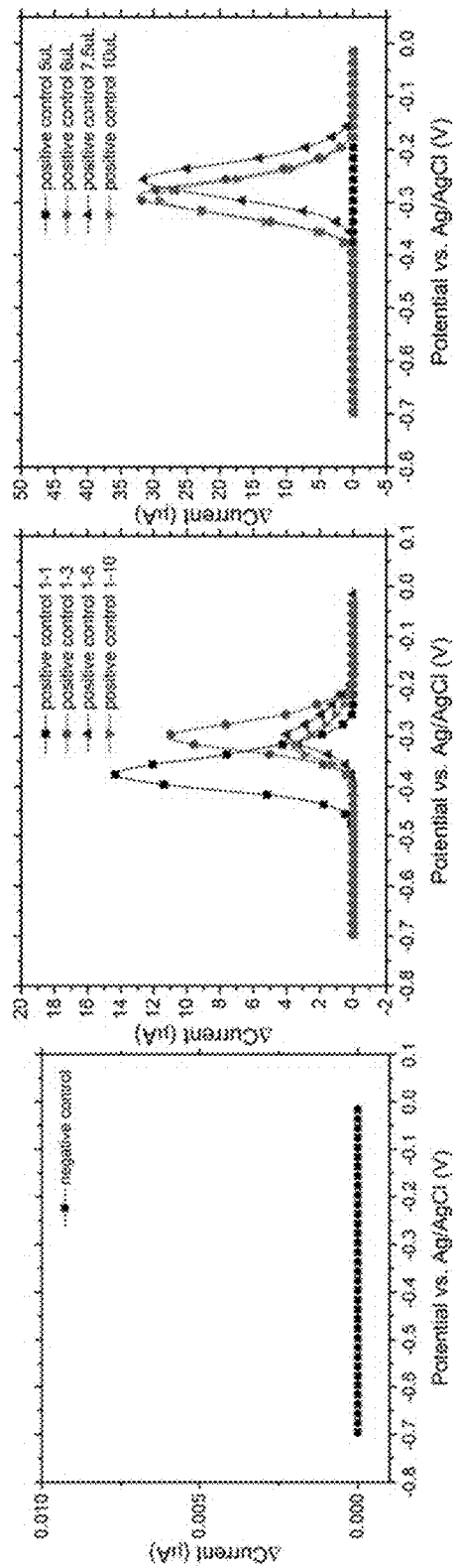
FIG. 7 illustrates baseline-subtracted square wave voltammograms of wound fluid exudate of FIG. 6 of negative control (left), positive controls (middle), and positive control at different volumes (right).

Each clinical sample was run in duplicate with a new sensor being used each time. The investigators were blinded to the microbiome 16SrRNA results at the time of the sensor detection experiment. The data was analyzed by two independent investigators using OriginPro 9.1 (OriginLab Corporation). Baselines were created for each data set using spline interpolation with 32 base points. The resulting baseline-subtracted data set was used to identify peaks in the current and to determine the maximum currents of those peaks (FIG. 4). From these maximum current values, using a cutoff of 0.030 µA, a binary determination was made for whether the probe was detecting pyocyanin (positive) or not (negative) (Table 2).

TABLE 1

Demographic and clinical characteristics of patients (n = 12) from whom wound fluid samples were tested. Wound size (mean ± SD) of all wounds with specimens collected (n = 14).

| | All patients n = 12 | *Pseudomonas* spp. positive on 16SrRNA n = 6 | *Pseudomonas* spp. negative on 16SrRNA n = 6 | p-value |
|---|---|---|---|---|
| Age (years, mean ± SD) | 50.76 (±17.14) | 49.85 (±11.57) | 51.67 (±22.55) | 0.8642 |
| Male sex (n, %) | 8 (66%) | 4 (66%) | 4 (66%) | 1.00 |
| Race | | | | |
| African American (n, %) | 8 (66%) | 5 (83%) | 3 (50%) | 0.3998 |
| Caucasian (n, %) | 3 (25%) | 1 (16.7%) | 2 (33.3%) | |
| Asian (n, %) | 1 (8.3%) | | 1 (16.7%) | |
| Smoking | | | | |
| Past | 5 | 2 | 3 | 1.00 |
| Never | 7 | 4 | 3 | |
| Current | 0 | 0 | 0 | |
| Diabetes | 4 | 2 | 2 | 1.00 |
| Renal disease | 2 | 1 | 1 | 1.00 |
| Wound surface area (cm², mean ± SD) | 85.41 (±177.3) | 14.13 (±12.77) | 146.5 (±230.9) | 0.19 |

TABLE 2

Experimental determinations (Positive/Negative) for whether clinical samples contained *Pseudomonas aeruginosa* based on peak currents obtained from electrochemical square-wave voltammograms.

| Sample | Peak current (μA) | Determination using 0.030 μA threshold cutoff | 16SrRNA sequencing results | 16SrRNA sequencing results (% relative abundance) |
|---|---|---|---|---|
| 10000111243072303-01A | 0.0000 | Negative | Negative | 0 |
| 10000111243072303-01B | 0.0000 | | | |
| 10000281244182304-01A | 0.1792 | Positive | Negative | 0 |
| 10000281244182304-01B | 0.0000 | | | |
| 10000281245152307-01A | 0.0000 | Positive | Positive | 0.0479 |
| 10000281245152307-01B | 0.0743 | | | |
| 10000281245152307-01C | 0.0094 | | | |
| 10000361152152303-01A | 0.0360 | Negative | N/A | N/A |
| 10000361152152303-01B | 0.0000 | | | |
| 10000371347232399-01A | 0.1241 | Positive | Positive | 0.0558 |
| 10000371347232399-01B | 0.0517 | | | |
| 10001641245022307-01A | 0.2263 | Positive | Positive | 0.0005 |
| 10001641245022307-01B | 0.2309 | | | |
| 10001681243072302-01A | 1.3491 | Positive | Positive | 0.0027 |
| 10001681243072302-01B | 0.9303 | | | |
| 10002511245142301-01A | 0.0195 | Negative | Positive | 0.0005 |
| 10002511245142301-01B | 0.0163 | | | |
| 10003031250192307-01A | 0.0000 | Negative | Positive | 0.9779 |
| 10003031250192307-01B | 0.0000 | | | |
| 10003131248152301-01A | 0.0090 | Negative | Negative | 0 |
| 10003131248152301-01B | 0.0280 | | | |
| 10003551344182399-01A | 0.0000 | Negative | Negative | 0 |
| 10003551344182399-01B | 0.0201 | | | |
| 10003841344182301-01A | 0.0757 | Positive | Negative | 0 |
| 10003841344192301-01A | 0.0469 | Positive | Negative | 0 |
| 10003841344192301-01B | 0.0539 | | | |
| 10003961346272308-01A | 0.0000 | Negative | Negative | 0 |
| 10003961346272308-01B | 0.0000 | | | |
| 10004351351142399-01A | 0.6262 | Positive | Positive | 0.2478 |
| 20000721546162301-06 wf volume test 6 μL | 0.6232 | Positive | Positive | N/A |
| 20000721546162301-06 wf volume test 7.5 μL | 4.3056 | | | |

Statistical Analysis

Data was analyzed using GraphPad Prism 5.03 (for Windows, GraphPad Software, San Diego Calif., USA). Fisher's exact test and Chi-squared tests were used for categorical variables and Student's t-test was used for continuous variables. Results are represented as mean±SD. A p value less than 0.05 indicate statistical significance; all significance tests were performed and interpreted in a two-sided manner.

Results obtained from the microbiome profile generated by 16S Ribosomal RNA sequencing were reviewed and samples with any positive *Pseudomonas* reads were considered to test positive for *Pseudomonas*. These results were compared to the results from the pyocyanin detector, and the sensitivity and specificity of the sensor was calculated.

Results

Paired wound effluent and biofilm samples were analyzed from 14 unique samples obtained from 12 patients (2 patients with serial samples collected at different time points were available). The mean age of patients was 50.18 years. Of the 14 samples subjected to microbiome profiling by 16SrRNA sequencing, 7 had detectable *Pseudomonas* spp. (sequencing positive). All 14 wounds were recalcitrant at the time of specimen collection.

There were no significant differences in age, sex, race, or comorbidities in the patients whose samples were positive for *P. aeruginosa* using 16SrRNA sequencing compared to those that were negative (Tables 1-2). Wounds that were positive for *P. aeruginosa* using 16SrRNA sequencing tended to be larger but this did not reach statistical significance.

A positive test on the pyocyanin detector was considered to be an oxidation peak around −0.25 V vs. a Ag/AgCl reference electrode with a cutoff of 0.030 μA. (Sismaet, H. J., T. A. Webster, and E. D. Goluch, *Up-regulating pyocyanin production by amino acid addition for early electrochemical identification of Pseudomonas aeruginosa*. Analyst, 2014. 139(17): p. 4241-6. Bellin, D. L., et al., *Integrated circuit-based electrochemical sensor for spatially resolved detection of redox-active metabolites in biofilms*. Nat Commun, 2014. 5: p. 3256.) Data was analyzed as the mean of duplicates. Of the 14 samples, 8 tested positive using the pyocyanin detector cutoff of 0.030 μA.

Sensitivity and specificity of the pyocyanin probe for detecting the samples that contained *Pseudomonas* spp. based on microbiome sequencing and results are reported in Table 3. The probe tested positive in 5 out of 7 samples that were positive for *Pseudomonas* on 16SrRNA sequencing and was negative on 4 out of 7 samples with negative 16SrRNA results, giving a sensitivity of 71% (95% CI 0.29-0.96) and specificity of 57% (95% CI 0.18-0.90).

TABLE 3

Sensitivity and specificity of pyocyanin probe compared to 16SrRNA sequencing for *Pseudomonas* spp. Data analyzed using Fisher's exact test.

|  | 16SrRNA positive | 16SrRNA negative |
| --- | --- | --- |
| Pyocyanin sensor positive | 5 | 3 |
| Pyocyanin sensor negative | 2 | 4 |

| Sensitivity (95% CI) | Specificity (95% CI) | Positive predictive value (95% CI) | Negative predictive value (95% CI) |
| --- | --- | --- | --- |
| 0.71 (0.29-0.96) | 0.57 (0.18-0.90) | 0.62 (0.25-0.91) | 0.66 (0.22-0.95) |

The pyocyanin probe was simple to use and had high inter-observer agreement regarding interpretation of a positive result. When compared with a diagnostic gold-standard of 16SrRNA sequencing, the pyocyanin probe had a sensitivity of 71% and specificity of 57% indicating that it may be useful as a point-of-care test in screening for presence of *Pseudomonas* in human wound fluid.

During probe development, one of the concerns raised about the utility of this probe for testing human samples was that there may be multiple other organisms generating other molecules which might interfere with probe performance. Human wound samples often have polymicrobial flora and this was indeed the case for the specimens reported here. The results reported showed no other redox peaks in the reference window for the pyocyanin probe. This indicates that despite presence of multiple other organisms in human specimens, there do not appear to be other redox-active molecules that would impede the probe performance in a clinical setting. However, small potential shifts were observed in where the pyocyanin peak occurred. This may be attributed to differences in the salt and pH concentration of the sample media, and the limited stability of the Ag/AgCl quasi-reference electrode of the disposable sensor.

It was found that most of the samples containing *P. aeruginosa* tested pyocyanin positive using the present electrochemical approach. By lowering the cutoff maximum current determination, the sensor's sensitivity could have been improved to 85.7% while decreasing specificity to 42.9%. The detection limit of electrochemical sensors can be improved by switching to micro and nano-fabricated electrodes. (Zevenbergen, M. A., et al., *Stochastic sensing of single molecules in a nanofluidic electrochemical device.* Nano Lett, 2011. 11(7): p. 2881-6.)

The testing revealed some false negative results using the pyocyanin probe. While pyocyanin is a very specific molecule, produced only by *Pseudomonas*, there are some environments even in in vitro culture of *Pseudomonas* in which pyocyanin production is low. It is possible that the wound microenvironment may have impacted pyocyanin production in some of the clinical cases studied here.

Additionally, the sample size is small because this was a pilot study designed to be hypothesis generating. Also, while the 16SrRNA testing is a good gold standard test for determination of bacterial presence in the wound and relative abundance of specific bacteria relative to the entire microbiome profile of the specimen, 16SrRNA testing alone does not give information regarding the quantitative abundance of a particular bacterium in one specimen relative to other specimens. It is possible that some of the false positives and false negatives in this study are attributable to very low *Pseudomonas* abundance in the sample and further testing is needed to understand the clinical relevance of false positive and false negative tests as this device is further refined and developed with a view to clinical indications. In addition, 16SrRNA does not discriminate between *Pseudomonas* species whereas the pyocyanin probe will only detect the presence of *Pseudomonas aeruginosa*. Taking this into account potentially explains one of our false negatives, where the sequencing may be indicating the presence of *Pseudomonas* species other than *aeruginosa*.

The results from this study provide useful and unexpected data regarding detection of *P. aeruginosa* in clinical samples and validate this electrochemical approach as a rapid point-of-care diagnostic.

EXAMPLE 2

A study was conducted to look at the killing of cells inside of a *P. aeruginosa* biofilm (grown in a microfluidic environment) via detected PYO, using SWV at a disposable three electrode cell, when exposed to different concentrations of the antibiotic colistin sulfate.

The condition of cells in *Pseudomonas aeruginosa* biofilms was monitored via the electrochemical detection of the electro-active virulence factor pyocyanin in a fabricated microfluidic growth chamber coupled with a disposable three electrode cell. Cells were exposed to 4, 16, and 100 mg/L colistin sulfate after overnight growth. At the end of testing, the measured maximum peak current (and therefore pyocyanin concentration) was reduced by approximately 68% and 82% in *P. aeruginosa* exposed to 16 and 100 mg/L colistin sulfate, respectively. Samples were removed from the microfluidic chamber, analyzed for viability using staining, and streaked onto culture plates to confirm that the *P. aeruginosa* cells were affected by the antibiotics. The correlation between electrical signal drop and the viability of *P. aeruginosa* cells after antibiotic exposure highlights the usefulness of this approach for future low cost antibiotic screening applications.

Materials and Methods

*P. aeruginosa* strain PA14 and m-cherry *Escherichia coli* strain K12 were used for all antibiotic tests performed. Trypticase soy broth (BD 211768) was used as the nutrient source for all bacteria grown in these tests. Colistin sulfate (Adipogen AG-CN2-0065-G001) was dissolved in trypticase soy broth (TSB) at 1 g/L and used as a stock solution. When not in use, the stock solution was stored at 4° C. Polydimethylsiloxane (Ellsworth Adhesives 184 Sil. Elast. Kit 0.5 kg) was used to prepare all microfluidic devices. Disposable three electrode cells (Zensor TE100) were used for all measurements in this study. The electrochemical cells consist of carbon working and counter electrodes with a Ag/AgCl paste reference electrode. Tubing and luer lock fittings for microfluidic connections were purchased from Amazon Supply (B001GMWZM) and Value Plastic (MTLL230). To prevent bacteria from leaving the microfluidic growth chambers, Minisart RC4 0.2 micron regenerated cellulose luer lock syringe filters (17821K) were attached to the inlets and outlets of the devices via 19 gauge luer lock syringes (NE192PL-25). A syringe pump (Harvard Apparatus Fusion 200 211097) was used to control the flow rate of growth media and antibiotic through the microfluidic chamber. Electrochemical measurements were made using a multipotentiostat (CHI 1040C A2728).

Figure 9A:
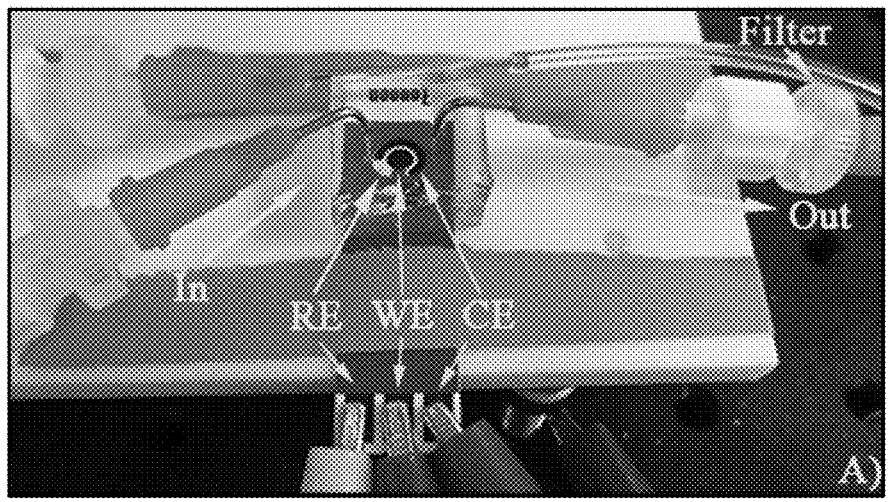
FIGS. 9A, 9B, and 9C illustrate experimental apparatus used in monitoring the susceptibility of Pseudomonas aeruginosa biofilms. A) Finished device connected to a potentiostat. Inlets and outlets contain filters (pore size 0.2 μm) to prevent PA14 from leaving the channels. B) Schematic of the sensor covered with a microfluidic chamber (not to scale). Bacteria are trapped in the chamber while fluid moves in and out. C) Scanning electron micrograph (SEM) of PA14 grown on top of the carbon working electrode after overnight growth under stagnant conditions. Reference, Working, and Counter Electrodes (RE, WE, and CE, respectively).
Figure 9B:
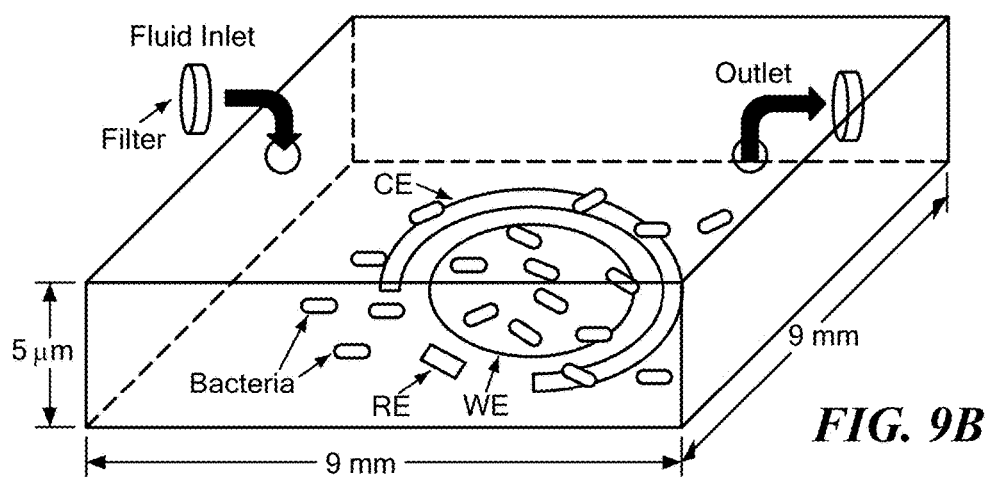
Figure 9C:
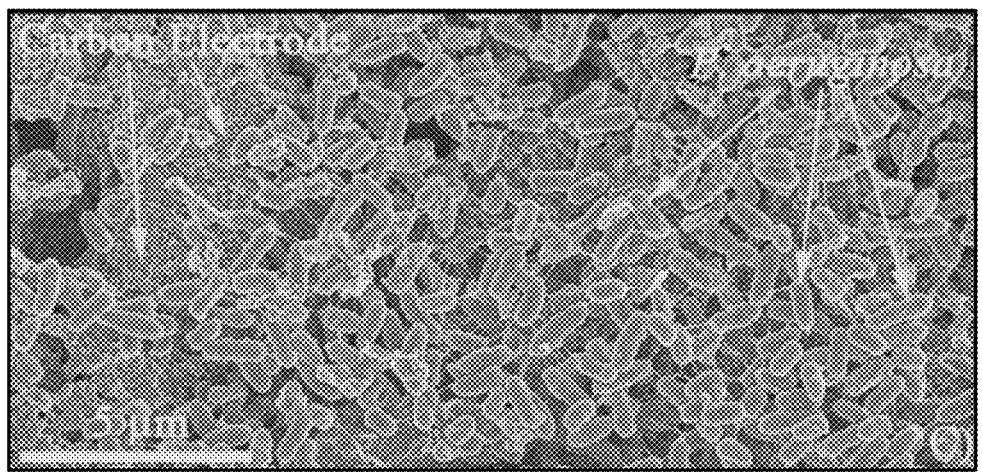

Polydimethylsiloxane (PDMS) wells were fabricated from 9 mm×9 mm tape molds made on glass slides (3M Scotch Tape, tape thickness ≈50 μm) using a standard method. (A. B. Shrirao and R. Perez-Castillejos, Simple fabrication of microfluidic devices by replicating scotch-tape masters, *Chips Tips,* 17 May 2010.) The PDMS wells had a final volume of approximately 4 μL and were designed to cover the entire electrochemical cell (FIG. 9A). Inlets and outlets in the wells were drilled and the resulting microfluidic devices were fabricated by irreversibly bonding PDMS to the disposable electrochemical cells using air plasma (Anatech SP-100, 5-7 s at 100 W). The microfluidic channels were filled with trypticase soy broth (TSB) at a flow rate of 10 μL/min. To facilitate complete filling of the chamber (removal of air bubbles), an empty syringe was attached to the outlet. By pulling and releasing vacuum on the outlet, TSB was pulled through the chamber displacing any air bubbles.

For antibiotic testing, cultures of PA14 and *E. coli* were grown over night in 3 mL of TSB (concentration approximately $10^{11}$ cells/mL). After overnight growth, samples were centrifuged for 3 min at 10,000 rpm. The supernatant was discarded and the cultures were reconstituted in 3 mL of fresh TSB. After removing the inlet syringe filter, approximately 24 μL of reconstituted cell culture was loaded into the growth chamber at a flow rate of 10 μL/min. At this flow rate the velocity in the chamber was such that PA14 could not resist flow (*P. aeruginosa* speed ≈30-50 μm/s), while the outlet filter prevented cells from exiting. (T. S. Murray and B. I. Kazmierczak, *J Bacteriol,* 2006, 188, 6995-7004.) After loading cells, the filter was replaced, sealing the bacteria into the growth chamber. Biofilms were then allowed to grow at room temperature overnight under stagnant conditions. Stagnant conditions were chosen to ensure that the cells had ample time to adhere to the surface and form a biofilm over the sensor. After overnight growth, flow at 0.1 μL/min was initiated with either TSB or colistin sulfate in TSB and the electrochemical response was monitored. (K. P. Kim, Y. G. Kim, C. H. Choi, H. E. Kim, S. H. Lee, W. S. Chang and C. S. Lee, *Lab Chip,* 2010, 10, 3296-3299.)

Samples were scanned from −0.5 to 0.2 V versus the internal Ag/AgCl reference electrode on the disposable electrochemical cell (Zensor). Square wave voltammetry (SWV) was used at an amplitude voltage of 50 mV and a frequency of 15 Hz. SWV was chosen due to its increased sensitivity and its ability to monitor the electrochemical peak of PYO compared to other voltammetric and amperometric techniques. (L. Pires, K. Sachsenheimer, T. Kleintschek, A. Waldbaur, T. Schwartz and B. E. Rapp, *Biosens Bioelectron,* 2013, 47, 157-163. A. J. Bard and L. R. Faulkner, *Electrochemical methods fundamentals and applications,* John Wiley & Sons Inc., 2011.)

Figure 13:
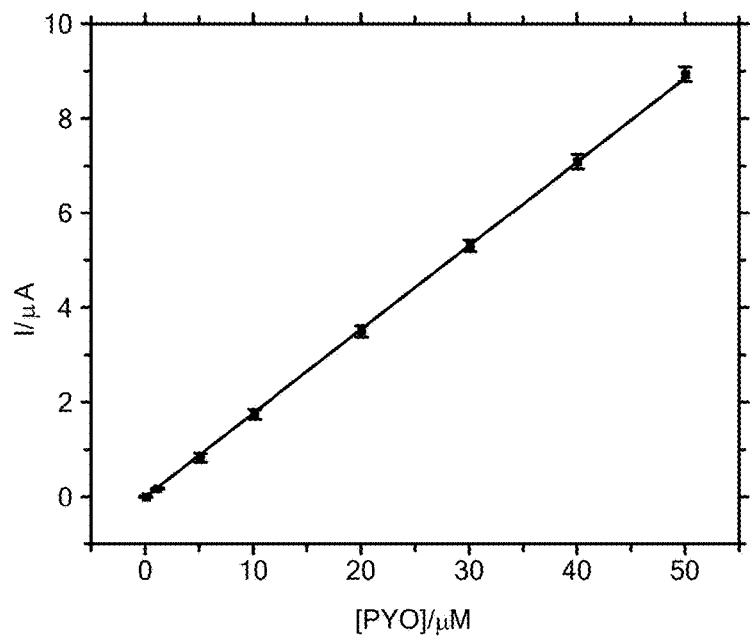
FIG. 13 illustrates maximum current from SWVs of pyocyanin in 30 g/L TSB from 0 to 50 μM. SWVs were performed from −0.5 to 0 V at a frequency of 15 Hz and an amplitude voltage of 50 mV. Linear fit: $I/\mu A=0.18[PYO]/\mu M$; where I=current and [PYO]=concentration of pyocyanin in TSB.

A calibration curve for PA14 grown in trypticase soy broth (TSB) was obtained, as illustrated in FIG. 13. More particularly, square wave voltammograms for concentrations of pyocyanin from 0 to 50 μM were obtained using three different disposable Zensor electrodes. The dilution series was repeated twice and each concentration was scanned three times per disposable electrode. The average maximum current for both runs through the dilution series was averaged and plotted versus current. FIG. 13 illustrates a maximum current from SWVs of pyocyanin in 30 g/L TSB from 0 to 50 μM. SWVs performed from −0.5 to 0 V at a frequency of 15 Hz and an amplitude voltage of 50 mV. A linear fit is $I/\mu A=0.18[PYO]/\mu M$; where I=current and [PYO]=concentration of pyocyanin in TSB.

PYO concentration was approximated from the calibration curve of PYO in TSB (FIG. 13). After loading the PDMS chambers with TSB, the sample was scanned 10 times and the average taken to get the mean response of the TSB. All subsequent measurements were then compared to this response. Three measurements were taken during the loading of the cells, with additional measurements taken every 30 min during the remainder of the tests. For each concentration of antibiotic tested, three different microfluidic setups were used.

Electrochemical measurements were processed by subtracting the baseline signal. One way analysis of variation (ANOVA) was used to determine the statistical significance of resulting measurements.

Samples were prepared for SEM imaging by fixing in a 2.5% glutaraldehyde (EMSDIASUM 16120) in a 0.1 M sodium cacodylate buffer (EMSDIASUM 11654). After fixing, samples were washed in cacodylate buffer, and then dehydrated in increasing concentrations of ethanol (Fisher BP2818-4 30-100%). After dehydration, ethanol was removed via critical point drying (Samdri-PVT-3D) using liquid $CO_2$. The final step in SEM preparation was plasma sputtering (Cressington Sputter Coater 208HR) 5 nm of palladium metal onto the samples making them conductive. Once prepared for imaging, samples were loaded into a Field Emission SEM (Hitachi S-4800) and probed at an acceleration voltage and emission current of 3 kV and 10 mA, respectively.

Cell viability after exposure to colistin sulfate was assessed using a LIVE/DEAD staining kit (EMD Chemicals Millipore 50-231-0606). Stains were prepared per manufacturer's operating procedure. After staining, 10 μL of sample was injected into an INCYTO C-chip disposable hemocytometer (DHC-N01). Cells were imaged using a fluorescence microscope, and the number of PA14 cells that were alive after exposure was determined using IMAGE J (ImageJ, U.S. National Institutes of Health, Bethesda, Md., USA, http://imagej.nih.gov/ij/).

Results

SWV were collected every 30 min from overnight cultures of PA14 in TSB, starting from the point at which they were loaded into the PDMS chambers, to determine whether electro-active molecules were being produced. *P. aeruginosa* continuously produces PYO as it grows, in both planktonic and biofilm phenotypes, which can be monitored electrochemically during the experiments. (D. Sharp, P. Gladstone, R. B. Smith, S. Forsythe and J. Davis, *Bioelectrochemistry,* 2010, 77, 114-119.) The utility of this approach is highlighted in FIG. 10 where the electrochemical response of PA14 grown in TSB is monitored over time.

Figure 14:
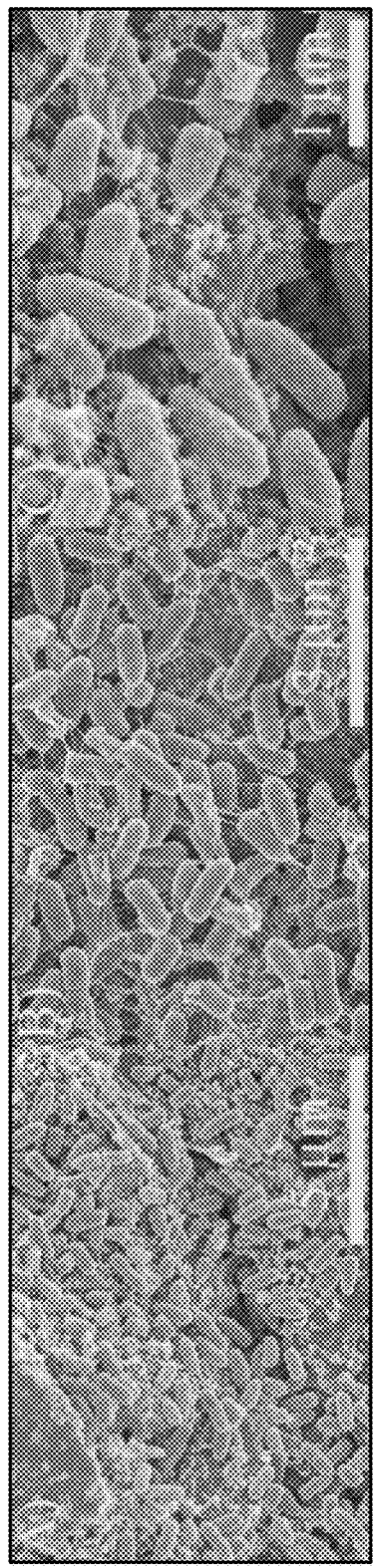
FIG. 14 illustrates SEM images of P. aeruginosa grown on the working electrode of a three electrode cell. From left to right, SEM images were taken at a magnification of 9,000×, 15,000×, and 30,000× at 3 kV. Note the presence of a large number of cells in all three images interlaced embedded in extracellular matrix.
Figure 15:
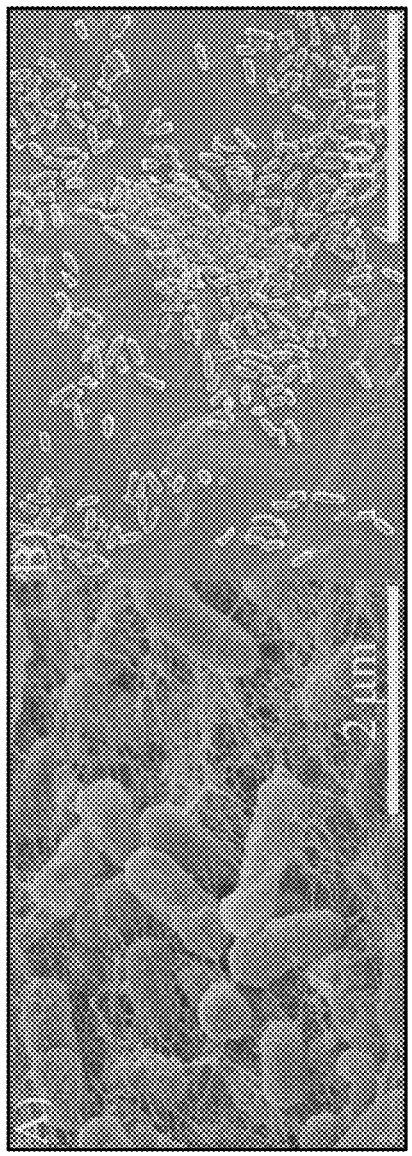
FIG. 15 illustrates SEM images of A) P. aeruginosa cells in the access hole of a PDMS device leading to the chamber area containing the sensor, and B) cells attached to the surface of the PDMS that forms the top of the sensing chamber.

(*P. aeruginosa* samples were prepared for SEM analysis to determine where in the growth chamber the bacteria were collecting. Samples were prepared by peeling the PDMS from the electrode and fixing the bacteria using a 2.5% glutaraldehyde in 0.1 M cacodyalate buffer (pH 7.2) at 4° C. for 2 hours. Samples were dehydrated in an increasing dilution series of ethanol and then critical point dried using liquid $CO_2$. Resulting SEMs are reported in FIGS. 14 and 15 and show the clear presence of biofilms growing in the chamber.)

Figure 10:
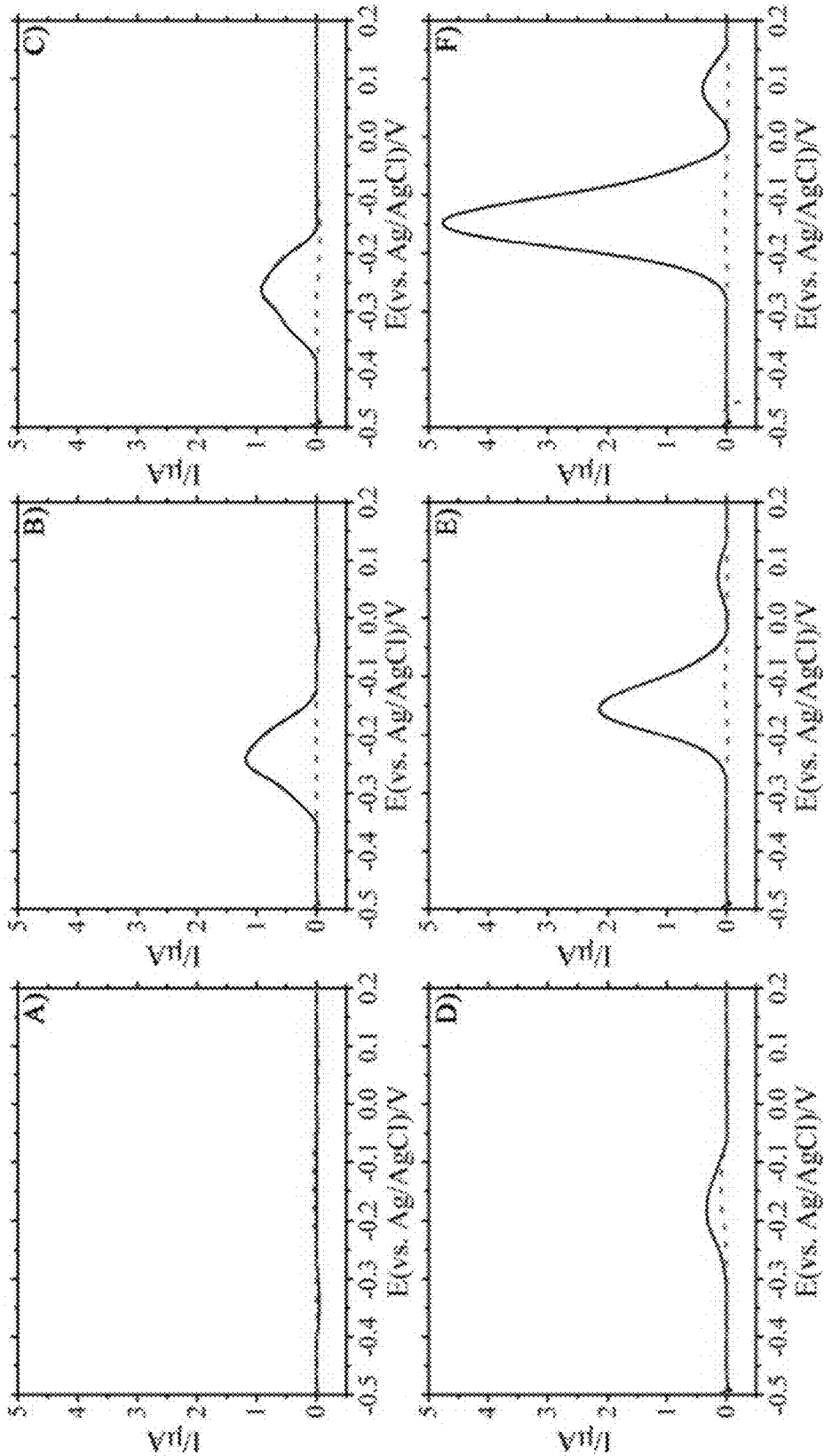
FIG. 10 illustrates square wave voltammetry (SWV) scans of PA14 and E. coli (solid and dashed lines respectively) cultured in trypticase soy broth (TSB) after loading 24 μL of overnight culture after A) 0 h, B) 12 h, C) 22 h, D) 35 h, E) 40 h, and F) 45 h. Flow of fresh TSB at 100 nL/min was initiated at 22 h. SWV scans performed from −0.5 to 0.2 V at a frequency of 15 Hz and an amplitude voltage of 50 mV.

The lack of observable peaks during loading indicated that no detectable PYO was present initially in the fresh TSB cell suspension (FIG. 10, graph A). As the biofilm formed under stagnant conditions, the oxidation peak height increased over time (FIG. 10, graphs A-B). SEM images of the PDMS growth chamber and the working electrode substrate showed bacteria carpeting both surfaces (see FIGS. 14 and 15) after overnight growth under stagnant conditions. Initiating the flow of fresh TSB into the channels after overnight growth allowed the biofilm to thrive. Indeed, the electrical signal increased after TSB flow was initiated (FIG. 2 graphs D-F), indicating the increased production rate of PYO. The presence of a second peak at later time points was observed. The first peak is due to PYO, while the appearance of a second peak is ascribed to the electrochemical reaction of a second phenazine derivative that has been reported in the literature as being 5-methylphenazine-l-carboxylic acid or one of its derivatives. (V. B. Wang, S. L. Chua, B. Cao, T. Seviour, V. J. Nesatyy, E. Marsili, S. Kjelleberg, M. Givskov, T. Tolker-Nielsen, H. Song, J. S. Loo and L. *PloS One*, 2013, 8, e63129. D. L. Bellin, H. Sakhtah, J. k. Rosenstein, P. M. Levine, J. Thimot, K. Emmett, L. E. Dietrich and K. L. Shepard, *Nat Commun*, 2014, 5, #3256.) The change in the oxidation potential, after the initiation of flow, where the peak current was measured can be attributed to the internal Ag/AgCl pellet used as the reference for these studies. Drift due to fluid flow is an unavoidable consequence of having the reference in direct contact with the test fluid. (M. W. Shinwari, D. Zhitomirsky, I. A. Deen, P. R. Selvaganapathy, M. J. Deen and D. Landheer, *Sensors*, 2010, 10, 1679-1715. 40. L. Rassaei, K. Mathwig, E. D. Goluch and S. G. Lemay, *J Phy Chem C*, 2012, 116, 10913-10916.) The measured peak potential stabilized over time with constant fluid flow and the peak current at this new potential was used for calculations. The movement of the peak over time can be observed in FIGS. 16-17. Measurement of the PA14 cultures with a traditional Ag/AgCl reference electrode (BASi MW-2030) showed that the PYO peak current appeared at the expected potential.

SWVs were taken every 30 minutes during exposure of cells to colistin sulfate. *Pseudomonas aeruginosa* and *Escherichia coli* were exposed separately to colistin sulfate at 4, 16, and 100 mg/L at a flow rate of 100 nL/min. Of interest is the complete lack of discernible peaks from SWVs for *E. coli* cells exposed to colistin sulfate compared to *P. aeruginosa* (FIGS. S5-S7). Scans are from one replicate but are representative all acquired scans.

While the overall electrical signal increased over time, a decrease was observed consistently at the initiation of fluid flow. There are two possibilities for the observed result. First, it can be an indicator of how firmly the biofilm has adhered to the surface of the microfluidic channel. The role of shear stress on cell adhesion has been studied previously; and, the results show that cells can be removed from surfaces at high shear stresses. (J.-C. Ochoa, C. Coufort, R. Escudié, A. Liné and E. Paul, *Chem Engin Sci*, 2007, 62, 3672-3684. Y.-P. Tsai, *Biofouling*, 2005, 21, 267-277.) As growth media flows through the channel it may remove bacteria if the biofilm is not firmly attached. (M. M. Salek, S. M. Jones and R. J. Martinuzzi, *Biofouling*, 2009, 25, 711-725.) The removal of bacteria in turn would lead to reduced production of PYO in the vicinity of the sensor (lowering the electrical signal). This is unlikely as the applied flow rates in this study are similar to those used by other groups and should be slow enough to avoid significant removal of the bacterial biofilm. (J. Kim, H. D. Park and S. Chung, Microfluidic approaches to bacterial biofilm formation, *Molecules*, 2012, 17, 9818-9834. K. P. Kim, Y. G. Kim, C. H. Choi, H. E. Kim, S. H. Lee, W. S. Chang and C. S. Lee, *Lab Chip*, 2010, 10, 3296-3299.)

Second, it is possible that the decrease in signal is due to PYO in solution being removed during flow, and it is only when a sufficiently large concentration of PYO is produced, to overcome convective transport, that the signal rebounds. Koley et al. (2011) demonstrated the presence of a PYO gradient (eletrocline) in biofilms of *P. aeruginosa* using scanning electro-chemical microscopy. (M. M. R. D. Koley, A. J. Bard, M. Whiteley, *Proc Nat Acad Sci USA*, 2011, 108, 19996-20001.) The authors showed that this electrocline extended hundreds of microns above the biofilm's surface. The change in the PYO electrocline due to fluid flow is likely responsible for the initial drop in signal when bulk fluid flow starts. Regardless, it is clear that even after the initiation of flow within the microfluidic chamber, the peak current remains indicating the cells are indeed growing within the chamber (FIGS. 11A, 11B, and 17-19). *E. coli* in TSB was used as a control since it is not expected to produce molecules that are redox-active in this voltage window. (D. Sharp, P. Gladstone, R. B. Smith, S. Forsythe and J. Davis, *Bioelectrochemistry*, 2010, 77, 114-119. T. A. Webster, H. J. Sismaet, J. L. Conte, I. P. J. Chan and E. D. Goluch, *Biosens Bioelectron*, 2014, 60, 265-270.) The lack of any discernible peak confirms that there are no electrochemical molecules produced by *E. coli* and that there is no contamination of the chambers by *P. aeruginosa* from the environment over the course of the experiment (see FIGS. 17-19). The absence of oxidation peaks from *E. coli* cells highlights the limitations of the proposed approach to electrochemically monitor the antibiotic susceptibility of other bacterial species. Alternatively, the ability to electrochemically measure the viability of PA14 by the production of PYO can be a useful selective marker of *P. aeruginosa* in patient samples. (T. A. Webster, H. J. Sismaet, J. L. Conte, I. P. J. Chan and E. D. Goluch, *Biosens Bioelectron*, 2014, 60, 265-270.) Furthermore the transparent nature of the PDMS used to fabricate growth chambers facilitates the use of fluorescent bacterial species and markers as reported in the literature. (J. Kim, H. D. Park and S. Chung, Microfluidic approaches to bacterial biofilm formation, *Molecules*, 2012, 17, 9818-9834. K. P. Kim, Y. G. Kim, C. H. Choi, H. E. Kim, S. H. Lee, W. S. Chang and C. S. Lee, *Lab Chip*, 2010, 10, 3296-3299.)

Figure 11A:
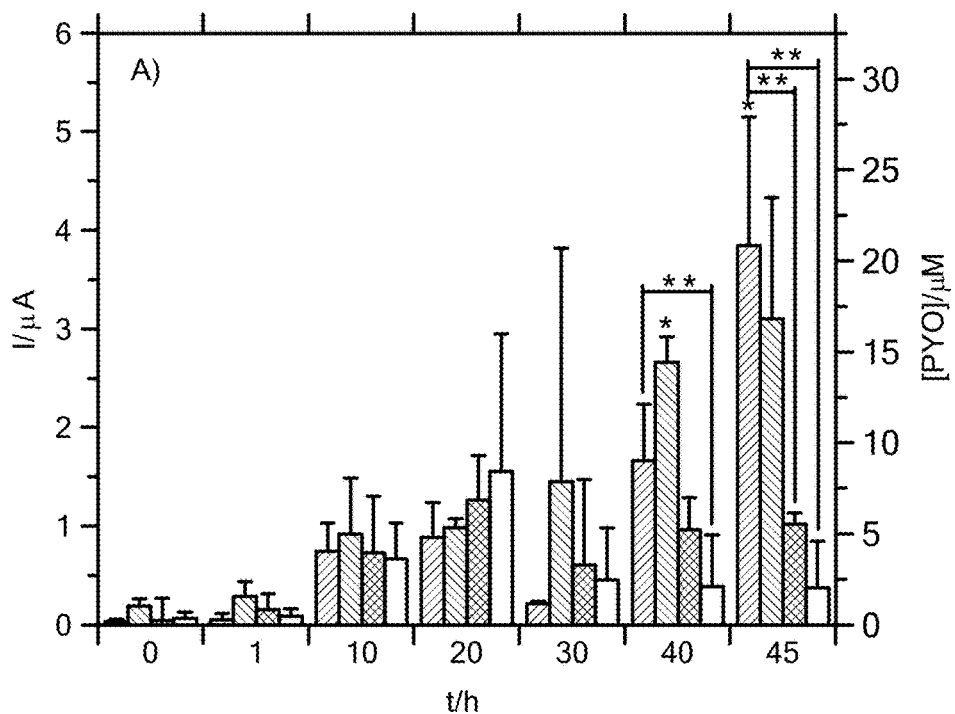
FIG. 11A illustrates response of PA14 biofilms at selected time points during the 48 hour experiments. Left axis: average peak current (blank subtracted) measured over time in PA14 cultures exposed to colistin sulfate at 0 (right slash), 4 (left slash, low MIC), 16 (crosses, High MIC), and 100 mg/L (no slash lines). Right axis: approximate pyocyanin concentration based on calibration curve. * indicates time points where only two replicates were used. ** indicates $P<0.05$ from ANOVA analysis.
Figure 16:
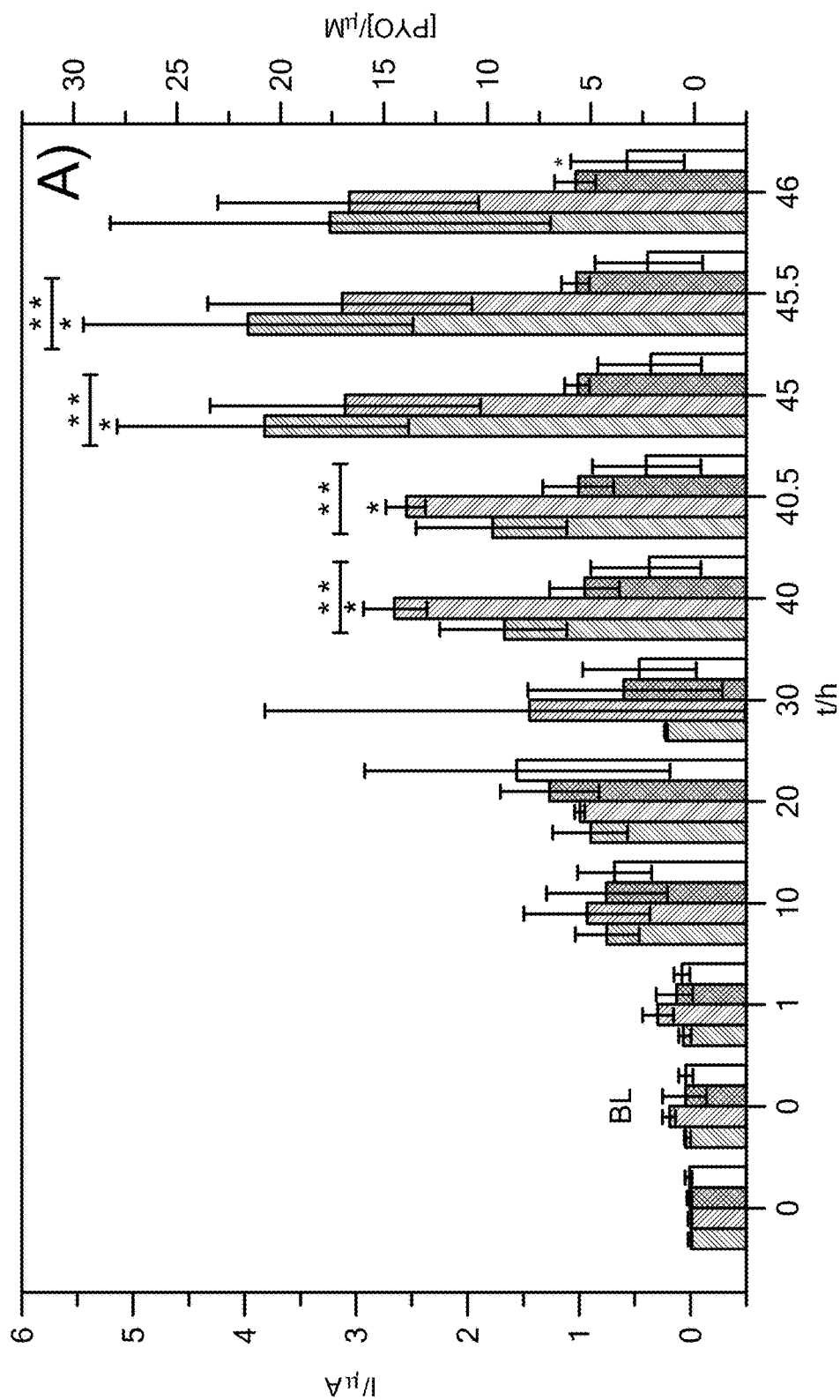
FIG. 16 illustrates response of PA14 biofilms at selected time points during the 48 hour experiments. (BL=Bacteria loaded into the chamber). Left axis: average peak current (blank subtracted) measured over time in PA14 cultures exposed to colistin sulfate at 0 (right slash), 4 (left slash, low MIC), 16 (crosses, High MIC), and 100 mg/L (no slash lines). Right axis: Approximate pyocyanin concentration based on calibration curve. * indicates time points where only two replicates were used. ** indicates $P<0.05$ from ANOVA analysis of 16 and 100 mg/L antibiotic concentrations against the control.
Figure 17:
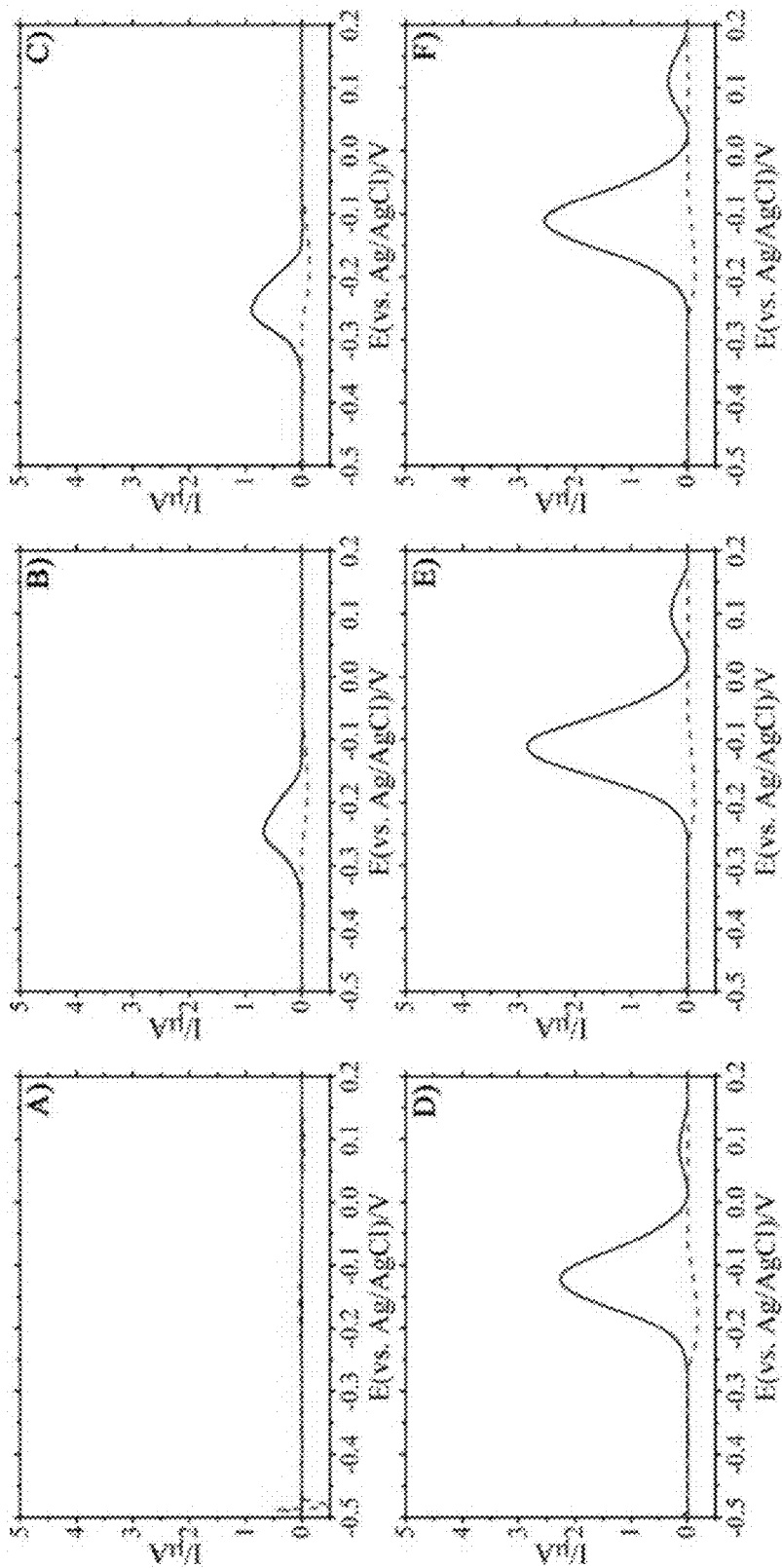
FIG. 17 illustrates SWVs of PA14 (solid lines) and E. coli (dashed lines) cultured in trypticase soy broth (TSB) after loading 24 μL of overnight culture after A) 0 h, B) 12 h, C)

After overnight growth of *P. aeruginosa*, 0.100 µL/min flow of colistin sulfate at 4, 16, and 100 mg/L in TSB was initiated. These concentrations were chosen to cover the range of colistin sulfate MIC values that are reported in literature. (J. M. Andrews, *J. Antimicrob Chemother*, 2001, 48, 5-16.) SWV measurements were taken to determine what effect the reported MIC concentrations of colistin sulfate (4 and 16 mg/L) have on PYO production. This, in turn, can be an indicator of *P. aeruginosa* biofilm susceptibility to colistin sulfate. Three devices per concentration of colistin sulfate were used and the average peak current reported (FIGS. 11A and 16). Error bars represent the standard deviation of the mean for three separate measurements at that time point, unless otherwise indicated. As a control, *E. coli* biofilms were exposed to the same concentrations of colistin sulfate. One replicate per concentration was performed for these tests. No oxidation peaks were observed for *E. coli* exposed to colistin sulfate signifying a lack of electrochemically active molecules (FIG. S2-S4). (D. Sharp, P. Gladstone, R. B. Smith, S. Forsythe and J. Davis, *Bioelectrochemistry*, 2010, 77, 114-119. E. Kim, T. Gordonov, W. E. Bentley and G. F. Payne, *Anal Chem*, 2013, 85, 2102-2108.)

Figure 11B:
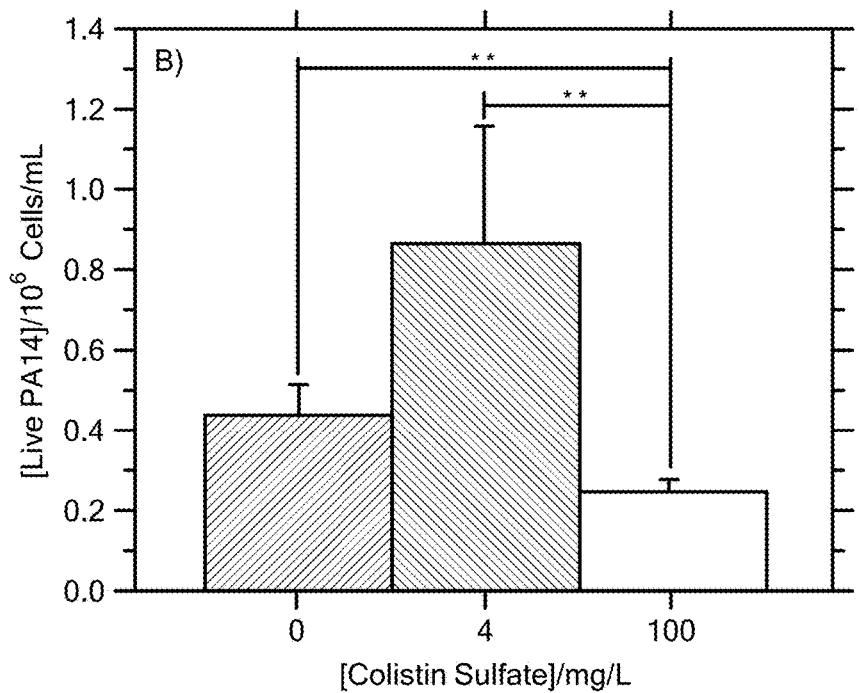
FIG. 11B illustrates live cell counts from PA14 after exposure to 0, 4, 100 mg/L colistin sulfate. Error bars are one standard deviation of mean for 3 samples. ** indicates $P<0.05$ from ANOVA analysis between the number of cells.

ANOVA was used to identify significant differences between the average peak currents of the three antibiotic concentrations and the control experiment without antibiotic (FIG. 11A). The analysis showed that the average peak current was significantly lower ($P<0.05$) for PA14 exposed to 16 and 100 mg/L colistin sulfate concentrations when compared against the control. The average percent decrease in the maximum peak current at the end of testing for PA14 exposed to 16 and 100 mg/L colistin sulfate was 68% and 82%, respectively, compared to the current produced by the cells in the control experiment. The average percent decrease in the measured current, compared to the control cells, was calculated by % Decrease=$100*(I_t-I_c)/I_c$ where $I_t$ equals the average peak current at time t and $I_c$ is the average peak current of the control *P. aeruginosa* cells. The decreased current response is directly related to a decrease in the measured PYO, indicating a correlation between the colistin sulfate concentration and PYO production. In contrast, the average response for cells treated with 4 mg/L colistin sulfate showed no significant difference when compared to biofilms exposed to only TSB, indicating that the lower MIC value was not significantly affecting the production of PYO. Importantly, FIGS. 11A and 11B show that continuous electrochemical monitoring allows the researcher to view the efficacy of an anti-pseudomonas antibiotic via a reduction in PYO production. FIG. 20 supports these results by demonstrating that PA14 exposed to ampicillin, an antibiotic that is not effective against this species, has no effect on PYO production. By reducing the amount of PYO produced by the bacteria, the host's body may be able to more effectively fight off the infection. (G. M. Denning, L. A. Wollenweber, M. A. Railsback, C. D. Cox, L. L. Stoll and B. E. Britigan, *Infect Immun*, 1998, 66, 5777.) (Regarding FIG. 20, PA14 cells were exposed to 100 mg/L of ampicillin under the same conditions as those subjected to 100 mg/L colistin sulfate exposure. A comparison of SWVs with the two antibiotics is shown in FIG. 20. Of note is that cells exposed to ampicillin continued to show an electrochemical response compared to those exposed to colistin sulfate. This was expected since ampicillin is known to be ineffective at killing *P. aeruginosa*.)

The inherent resistance of PA14 to the lowest MIC value used in this study could explain why the pyocyanin response did not significantly differ from blank measurements. Liquid samples of PA14 cultured on 4 mg/L colistin sulfate agar plates were able to grow indicating that this concentration had no effect on planktonic cell attachment and growth (FIG. 21). As such, it makes sense that biofilms of PA14 exposed to this concentration would not be affected and should produce similar levels of pyocyanin.

Regarding FIG. 21, liquid cultures of PA14, grown over night in 3 mL of TSB, were plated directly onto cetrimide agar plates containing 0, 4, and 100 mg/L of colistin sulfate. These plates were incubated overnight at 37° C. The plates were then inspected for bacterial growth (FIG. 21). Plates containing 0 and 4 mg/L colistin sulfate showed growth, whereas plates containing 100 mg/L colistin sulfate showed no colony formation. Colony formation at the lower MIC value of 4 mg/L colistin sulfate agrees with the results reported in FIGS. 11A, 11B, and 12.

The number of living cells measured after exposure to three different concentrations of colistin sulfate were compared (FIG. 11B). After the biofilm was exposed to antibiotic in the device, the PDMS chambers were peeled off and 100 µL of fresh TSB was spotted on the biofilm and pipetted vigorously to remove material from the surface of the electrode. Removed samples were used to measure live cell counts, performed with Millipore 3P Live/Dead Stain, using a haemocytometer. Each measurement was performed in triplicate and the error bars show one standard deviation of the mean. A concentration of approximately $4\times10^5$ live cells/mL was measured in the biofilms not exposed to colistin sulfate. Biofilms typically have lower concentrations of live cells than agitated liquid cultures. A statistically significant reduction in the number of live PA14 cells was measured for samples exposed to 100 mg/L colistin sulfate compared to cells exposed to 0 and 4 mg/L colistin sulfate. The ~2× reduction in the number of living cells supports the hypothesis that a reduction in the PYO signal is correlated with a reduction in the number of living cells. Recently, Connell et al. (2014) supported these findings as well by showing a correlation between the number of cells trapped in a chamber and the concentration of PYO that is present around the cells. (J. L. Connell, J. Kim, J. B. Shear, A. J. Bard, and M. Whiteley, *Proc Nat Acad Sci USA*, 2014, 111, 18255-18260.)

Figure 12:
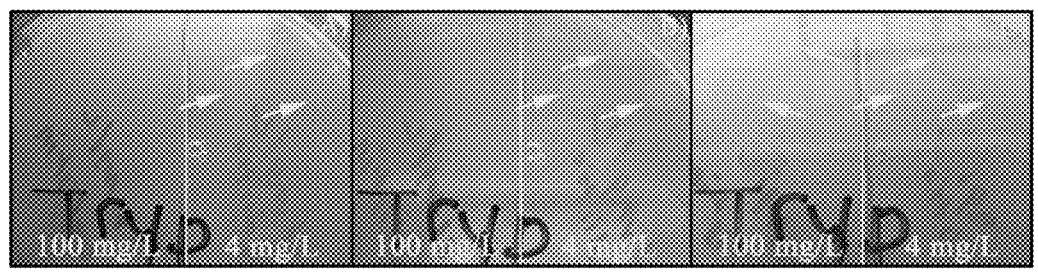
FIG. 12 illustrates PA14 exposed to 100 mg/L and 4 mg/L colistin sulfate for 20 hours within PDMS chambers then spotted onto TSB plates. Photographs of a plate after incubation at 37° C. for A) 4.3 h, B) 6.5 h, and C) 74.3 h (removed from the incubator after 24 h to avoid drying and grown at room temperature (≈23° C.)). Arrows highlight the locations of the first observed PA14 colonies. A vertical line divides the areas on the plate where PA14 exposed to 100 mg/L (left) and 4 mg/L (right) colistin sulfate were spotted.

FIG. 12 shows the culture results at three different time points for cells exposed to 4 and 100 mg/L colistin sulfate in microfluidic devices. Growth was observed in samples exposed to 4 mg/L colistin sulfate after only 4.3 h of incubation implying that this concentration had little effect on the cells' viability (FIG. 22). No growth was observed for cells exposed to 100 mg/L colistin sulfate after 6.5 h of incubation. Growth was observed for samples collected from chambers exposed to 100 mg/L colistin sulfate after 74 h, indicating that the complete elimination of viable bacteria from inside the chamber was not achieved. The qualitative results of the live cell stain are consistent with the culture plate experiments. The live cell concentration in biofilms exposed to 100 mg/L colistin sulfate (FIG. 11B), however, is higher than expected when compared to the reduced rate of colony formation on agar plates (FIG. 12). Taken together, these results suggest that the cells exposed to this antibiotic may have reduced their metabolic activity to make them less susceptible to the antibiotic.

Regarding FIG. 22, after exposure to colistin sulpahte at 4 and 100 mg/L flowing at 100 nL/min, the PDMS chambers were peeled from the disposable electrodes. A sterile loop was placed onto the electrodes, then streaked onto fresh TSB agar plates. Samples were incubated at 37° C., and monitored for growth. Cells exposed to 4 mg/L colistin sulfate began producing visible colonies after only 4 h of incubation. Over 24 h of incubation was required for colonies to form from cells exposed to 100 mg/L colistin sulfate. This indicates that cells were affected by the presence of colistin sulfate in solution at higher concentrations.

These results support the findings in the literature, drawing attention to the lower efficacy of reported MICs against microbial biofilms. (K. P. Kim, Y. G. Kim, C. H. Choi, H. E. Kim, S. H. Lee, W. S. Chang and C. S. Lee, *Lab Chip*, 2010, 10, 3296-3299.) It is clear from the results in FIGS. 11A, 11B, and 12 that a reduction in PYO production, under exposure to colistin sulfate, is correlated with a reduction in the viability of PA14. This reduction in pyocyanin and inhibited growth rate may allow a person's immune response to successfully fight off the bacterial infection. (L. Allen, D. H. Dockrell, T. Pattery, D. G. Lee, P. Cornelis, P. G. Hellewell and M. K. B. Whyte, J Immunol, 2005, 174, 3643-3649. L. R. Usher, R. A. Lawson, I. Geary, C. J. Taylor, C. D. Bingle, G. W. Taylor and M. K. B. Whyte, J Immunol, 2002, 168, 1861-1868. R. Wilson, T. Pitt, G. Taylor, D. Watson, J. Macadermot, D. Sykes, D. Roberts, and P. Cole, J Clin Invest, 1987, 79, 221-229.)

This study demonstrates, for the first time, the possibility of using electrochemical sensors to monitor metabolites produced by a biofilm that is exposed to antibiotics. The time to detection using this electrochemical approach (~45 h) is comparable to standard culture plate techniques. While simple identification of bacterial species can be accomplished within 24 hours, sensitivity tests required an additional 24-72 hours of incubation on several plates. Biochemical and molecular methods are available commercially that provide sensitivity information within minutes after the initial 24 hour colony formation period, but they require expensive reagents/instrumentation and additional sample processing. The analysis time of the proposed method may be lowered by employing miniature microfabricated electrochemical sensors that, in turn, allow for smaller microfluidic chambers to be employed compared to those utilized in this current study. Smaller chambers would potentially decrease the time to detection due to the confinement imposed on the cells.

In healthcare situations, such as wound infections, biofilms form rapidly and require immediate treatment. This approach can also be utilized to study biofilms that are more mature or exposed to any number of other experimental variables. Ultimately, an electrochemical sensor for susceptibility determination may be valuable for low-resource settings or for monitoring the status of infections in vivo while they are being treated with antibiotics.

It will be appreciated that the various features of the embodiments described herein can be combined in a variety of ways. For example, a feature described in conjunction with one embodiment may be included in another embodiment even if not explicitly described in conjunction with that embodiment.

The present invention has been described in conjunction with certain preferred embodiments. It is to be understood that the invention is not limited to the exact details of construction, operation, exact materials or embodiments shown and described, and that various modifications, substitutions of equivalents, alterations to the compositions, and other changes to the embodiments disclosed herein will be apparent to one of skill in the art.

What is claimed is:

1. A method of monitoring viability of a biofilm comprising *Pseudomonas aeruginosa* bacteria in a patient, the method comprising:
   (a) introducing a fluid sample from the patient into a microfluidic device including a working electrode and a reference electrode;
   (b) performing an electrochemical measurement to detect pyocyanin in the fluid sample; and
   (c) determining a concentration of pyocyanin in the fluid sample by using a previously determined correlation between pyocyanin concentration and current flow through the working electrode, the correlation comprising a linear relationship of increasing current flow with increasing pyocyanin concentration;
   wherein the pyocyanin concentration in the fluid sample provides a measure of the viability of the biofilm.

2. The method of claim 1, further comprising estimating a number of viable cells of *Pseudomonas aeruginosa* in the biofilm based on the concentration of pyocyanin determined in step (c).

3. The method of claim 1, wherein the electrochemical measurement is selected from the group consisting of squarewave voltammetry, linear sweep voltammetry, staircase voltammetry, cyclic voltammetry, normal pulse voltammetry, differential pulse voltammetry, and chronoamperometry.

4. The method of claim 3, wherein the electrochemical measurement is square wave voltammetry and the current flow is measured in response to one or more square wave potentials.

5. The method of claim 1, wherein:
   the microfluidic device comprises a second working electrode;
   the working electrode is one of an oxidizing electrode and a reducing electrode, and the second working electrode is the other of the oxidizing electrode and the reducing electrode; and
   the concentration of pyocyanin is measured as current flow through the oxidizing electrode and the reducing electrode.

6. The method of claim 1, wherein 10 μL or less of the fluid sample volume is introduced.

7. The method of claim 1, further comprising in step (a), continuously introducing the fluid sample into the microfluidic device.

8. The method of claim 7, further comprising repeating steps (a), (b), and (c).

9. The method of claim 1, wherein a capillary or wicking material is disposed at or near an inlet of the microfluidic device to draw the fluid sample into the device.

10. The method of claim 1, wherein the microfluidic device is worn by the patient or implanted in the patient.

11. The method of claim 1, wherein the microfluidic device is embedded in a wound dressing or within or adjacent to an absorbent pad for a wound dressing.

12. The method of claim 1, wherein the microfluidic device is present in a wound dressing, a bandage, a surgical implant, a catheter, a ventilator mask, a face mask, a surgical mask, an intubation tube, a contact lens case, a urine collection cup, or a urine bag.

13. The method of claim 1, wherein the fluid sample is from a human with cystic fibrosis, ventilator-associated pneumonia, a chronic wound, a burn wound, a surgical implant, or a surgical site.

14. The method of claim 1, wherein the fluid sample is a bodily fluid selected from the group consisting of wound exudate, bronchial lavage, sputum, urine, saliva, spinal fluid, tears, and blood.

15. A method of monitoring effectiveness of an antibiotic treatment of a *Pseudomonas aeruginosa* infection in a patient, the method comprising:
   (a) introducing a fluid sample from the patient into a microfluidic device including a working electrode and a reference electrode;
   (b) performing an electrochemical measurement to detect pyocyanin in the fluid sample; and
   (c) determining a concentration of pyocyanin in the fluid sample by using a previously determined correlation between known concentrations of the pyocyanin and a current flow through the working electrode, the correlation comprising a linear relationship of increasing current flow with increasing pyocyanin concentration;
   wherein the infection comprises the presence of a biofilm in the patient, the biofilm comprising *Pseudomonas aeruginosa*; and
   wherein the pyocyanin concentration in the fluid sample provides a measure of the effectiveness of the antibiotic treatment.

16. The method of claim 15, further comprising administering an increased dose of the antibiotic if the concentration of the pyocyanin is above a threshold level.

17. The method of claim 16, wherein the threshold level of pyocyanin is a concentration of at least 5 μM.

18. The method of claim 15, further comprising administering an increased dose of the antibiotic if the concentration of the pyocyanin does not drop below a threshold level after a predetermined time interval.

19. The method of claim 18, wherein the predetermined time interval is at least 12 hours.

20. The method of claim 18, wherein the threshold level of pyocyanin is a concentration of at least 5 µM.

21. The method of claim 15, further comprising administering a decreased dose of the antibiotic or stopping the antibiotic if the concentration of the pyocyanin drops below a threshold level.

22. The method of claim 21, wherein the threshold level of pyocyanin is a concentration of at least 5 µM.

23. The method of claim 15, wherein the antibiotic is colistin sulfate or ciprofloxacin.

* * * * *